(12) United States Patent
Bower et al.

(10) Patent No.: US 7,977,051 B2
(45) Date of Patent: Jul. 12, 2011

(54) EGIII-LIKE ENZYMES, DNA ENCODING SUCH ENZYMES AND METHODS FOR PRODUCING SUCH ENZYMES

(75) Inventors: Benjamin S. Bower, Pacifica, CA (US); Timothy Fowler, San Carlos, CA (US); Jay Ian Phillips, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 463 days.

(21) Appl. No.: 11/348,013

(22) Filed: Feb. 6, 2006

(65) Prior Publication Data

US 2007/0026420 A1    Feb. 1, 2007

Related U.S. Application Data

(63) Continuation of application No. 09/284,327, filed on Apr. 10, 1999, now abandoned.

(51) Int. Cl.
| | |
|---|---|
| C12Q 1/68 | (2006.01) |
| C12P 19/34 | (2006.01) |
| C12N 9/42 | (2006.01) |
| C07H 19/00 | (2006.01) |
| C07H 21/02 | (2006.01) |
| C07H 21/04 | (2006.01) |

(52) U.S. Cl. .......... 435/6; 435/91.1; 435/209; 536/22.1; 536/23.1; 536/23.2

(58) Field of Classification Search ............. 435/6, 91.1, 435/209; 536/22.1, 23.1, 23.2
See application file for complete search history.

(56) References Cited

U.S. PATENT DOCUMENTS

| | | | |
|---|---|---|---|
| 4,738,682 A | 4/1988 | Boegh et al. | 8/401 |
| 4,832,864 A | 5/1989 | Olson | 252/174.12 |
| 5,068,009 A | 11/1991 | Jokinen et al. | 162/9 |
| 5,246,853 A | 9/1993 | Clarkson et al. | 435/263 |
| 5,254,283 A | 10/1993 | Arnold et al. | 252/174.12 |
| 5,290,474 A | 3/1994 | Clarkson et al. | 252/174.12 |
| 5,475,101 A | 12/1995 | Ward et al. | 536/23.74 |
| 5,753,484 A * | 5/1998 | Ward et al. | 435/209 |
| 6,268,328 B1 * | 7/2001 | Mitchinson et al. | 510/392 |

FOREIGN PATENT DOCUMENTS

| | | |
|---|---|---|
| EP | 0220 016 B1 | 4/1987 |
| EP | 0271 004 B1 | 4/1993 |
| EP | 0 684 304 A2 | 11/1995 |
| FI | 87372 | 10/1990 |
| GB | 1368599 | 10/1974 |
| GB | 2075028 A | 11/1981 |
| GB | 2094826 | 9/1982 |
| GB | 2095275 A | 9/1982 |
| WO | WO 91/04673 | 4/1991 |
| WO | WO 92/16687 | 1/1992 |
| WO | WO 92/06209 | 4/1992 |
| WO | WO 94/14953 | 7/1994 |
| WO | WO 94/21801 | 9/1994 |
| WO | WO 94/28117 | 12/1994 |
| WO | WO 95/16360 | 6/1995 |
| WO | WO 97/43409 | 11/1997 |

OTHER PUBLICATIONS

Bennett & Lasure, "More Gene Manipulations in Fungi," *Academic Press*, San Diego, pp. 70-76 (1991).
Bergés, T. et al., "Isolation of uridine auxotrophs from *Trichoderma reesei* and efficient transformation with the cloned ura3 and ura5 genes" *Curr. Genet.*, vol. 19, pp. 359-365 (1991).
Henrissat, B., "A Classification of Glycosyl Hydrolases based on Amino Acid Sequence Similarities," *Biochemical Journal*, V. 280, 1991, pp. 309-316.
Hreggvidsson et al., "An Extremely Thermostable Cellulase from the Thermophilic Eubacterium Rhodothermus marinus," *Appl. Environ. Microb.*, vol. 62, No. 8, pp. 3047-3049 (1996).
Kitamoto et al., "Molecular cloning, purification and characterization of two endo-1, 4-beta-glucanases from *Aspergillus oryzae* KBN616," *Applied Microbiology and Biotechnology*, V. 46 No. 5-6, 1996 pp. 538-544.
Knowles et al., "Cellulase families and their genes," TIBTECH, V. 5, 1987, pp. 255-261.
Mizobuchi et al., "Rapid Amplification of Genomic DNA Ends," *Circle Reader Service* No. 143, 15(2): 215-216 (1993).
Ooi et al., "Cloning and sequence analysis of a cDNA for cellulase ( FI-CMCase) from *Aspergillus aculeatus*," Curr. Genet., vol. 18, pp. 217-222 (1990).
Saarilahti et al., "CeIS: a novel endoglucanase identified from *Erwinia carotovora* subsp. *carotovora*," *Gene*, vol. 90, pp. 9-14 (1990).
Sakamoto et al., "Cloning and sequencing of cellulase cDNA from *Aspergillus kawachii* and its expression in *Saccharomyces cerevisiae*," *Curr. Genet.*, vol. 27, pp. 435-439 (1995).
Sambrook et al., Molecular Cloning: A Laboratory Manual, New York: Cold Spring Harbor Press, 1989.
Sheir-Neiss et al., "Characterization of the Secreted Cellulases of *Trichoderma reesei* Wild Type and Mutants During Controlled Fermentations" *Appl. Microbiol. Biotechnol.* 20:46-53 (1984).
Suominen et al., "*Trichoderma reesei* Cellulases and other Hydrolases," Proceedings of the Tricel93 Symposium Jun. 2-5, 1993, Espoo, Finland, Foundation for Biotech. and Indust. Fermentation Research, vol. 8, pp. 153-158 (1993).
Wittmann S. et al., "Purification and characterization of the CelB Endoglucanase from Streptomyces lividans 66 and DNA sequence of the Encoding Gene," *Applied and Environmental Microbiology*, V. 60 N. 5, 1994, pp. 1701-1703.
Wood et al, "Methods in Enzymology," vol. 160, pp. 87-112 (1988).
PCT Search Report, Nov. 6, 1999.

* cited by examiner

*Primary Examiner* — Ganapathirama Raghu

(57) ABSTRACT

The present invention is directed to cellulase compositions which share unique highly conserved regions with a known useful cellulase. More specifically, the present invention relates to a series of newly discovered enzymes from fungi and bacteria which are related by virtue of having at least one of five important conserved amino acid sequences which are also present in EGIII.

20 Claims, 8 Drawing Sheets

Amino Acid Sequence of EGIII

MKFLQVLPALIPAALAQTSCDQWATFTGNGYTVSNNLWGASAGSGFGCVTAVSLSGGAHADW
QWSGGQNNVKSYQNSQIAIPQKRTVNSISSMPTTASWSYSGSNIRANVAYDLFTAANPNHVT
YSGDYELMIWLGKYGDIGPIGSSQGTVNVGGQSWTLYYGYNGAMQVYSFVAQTNTTNYSGDV
KNFFNYLRDNKGYNAAGQYVLSYQFGTEPFTGSGTLNVASWTASIN

FIGURE 1

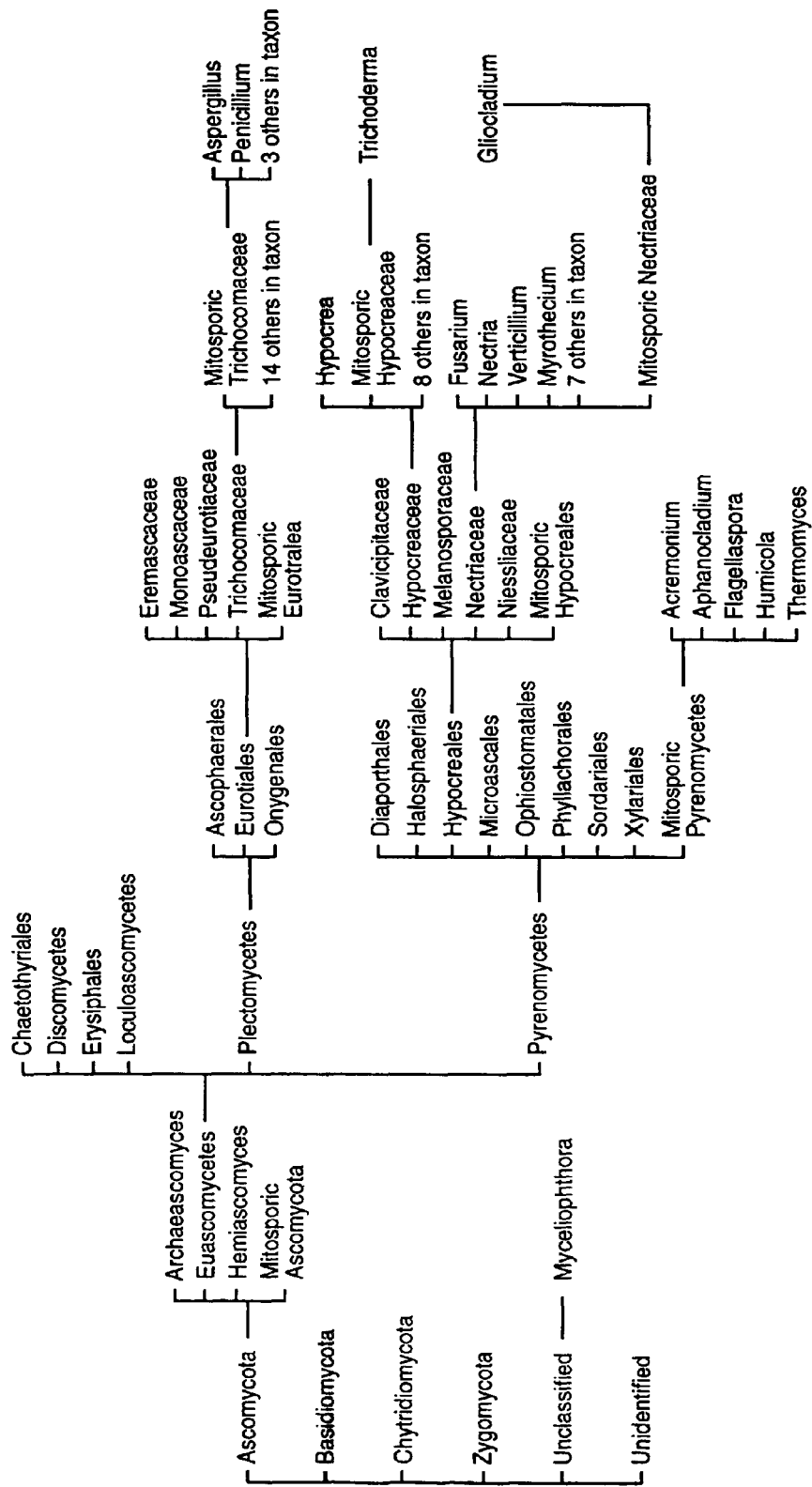
FIG._2

```
             NNLWGKDSG--GSQCTTVDSLSDGGI-SWSTAWSWSGGEGNVKSYPNS------GLQFSAGKK-VSSISS
             ---------|---------|---------|---------|---------|---------|---------|
                     10        20        30        40        50        60        70
EG3IN.PRO    NNLWGASAGS-GFGCVTAVSLSG-GA-SWHADWQWSGGQNNVKSYQNS------QIAIPQ-KRTVNSISS 60
FUSEQIN.PRO  NNFWGKDSGT-GDQCTHVNWNNANGA-GWDVEWNWSGGKDNVKSYPNS------ALLIGEDKKTISSITN 62
GLIOIN.PRO   NNKWGQGSGS-GSQCLTIDKTWDSNV-AFHADWSWSGGTNNVKSYPKR------RSEFSRGKK-VSSIGT 61
ACRHYPO.PRO  ---WGPRSAESGEQCTTNNGLSDDGTLSWSVEWTWVGAPSSVKSYPN--------VFVEAEPRPLSEVSS 59
ASPKAWA1.PRO QNLWGEYQGT-GSQCVYVDKLSSSGA-SWHTKWTWSGGEGTVKSYSNS------GLTF-D-KKLVSDVSS 60
ASPACU1.PRO  NNLWGKDAGS-GSQCTTVNSASSAGT-SWSTKWNWSGGENSVKSYANS------GLTF-N-KKLVSQISQ 60
HUMIN.PRO    NNLWGKDTATSGWQCTYLDGTNNGGI-QWSTAWEWQGAPDNVKSYPYV------GKQIQRGRK-ISDINS 62
11AG8IN.PRO  NNRWGTSAT----QC----INVTGNGFEITQADGSVPTNGAPKSYPSVYDGCHYGNC-APRTTLPMRISS 61
ERWCARIN.PRO NNVWGKDEI----KG-WQQTIFYNSPISMGWNWHWPSSTHSVKAYPSLVSGWHWTAGYTENSGLPIQLSS 65
GLIO314.PRO  NNLWGMGSGS-GSQCTYVDKVWAEGV-AWHTDWSWSGGDNNVKSYPYS------GRELGTKRI-VSSIKS 61
GLIO3HYP.PRO NNLWGQDNG-SGSQCLTVEGVTDGLA-AWSSTWSWSGGSSSVKSYSNA------VLSAEAAR--ISAISS 60
HGRIS.PRO    NNLWGQDTATSGWQCTYLDGTNNGGI-QWSTAWEWQGAPDNVKSYPYV------GKQIQRGRK-ISDINS 62
RHMARIN.PRO  NNVWGAETA----QC--IEVGLETGNFTITRADH--DNGNNVAAYPAIYFGCHWAPARAIRDCAARAGAV 62
SLIVIN.PRO   NNRWGSTAP----QC----VTATDTGFRVTQADGSAPTNGAPKSYPSVFNGCHYTNC-SPGTDLPVRLDT 61
PENNOT.PRO   ---WGKDSGS-GSQCASVNSISDSGV-SWSTIWNWSGGEDNVKSYPNS------GLVALK-KQPVSDISS 58
PHANHYPO.PRO ---WGKDSG-TGSQCLTVDGISSGLL-KWSATWSWSGGPYNVKSYPNA------VLQAPAAR--ASAISS 57
F42HYPO.PRO  -----S-------QCTTFESLSGNTI-VWNTKWSWSGGQGQVKSFANA------ALQFTPKK--LSSVKS 49
EMDESHYP.PRO NNLWGXDNADSGSQCTGVDSANGNSI-SWHTTWSWSGGSSSVKSYANA------AYQFTSTK--LNSLSS 61
MYCINS.PRO   ------------------------------------------------------------------------
CHBRAS.PRO   NNFWGQSRATSGSQCTYLDSSSNSGI-HWHTTWTWEGGEGEVKSYAYS------GRQVSTGLT-IASIDS 62

IPSSASWV-YSGTDIRA-NVAYDL-FTAADPNHATSSGDYELMIW
             ---------|---------|---------|---------|
                     80        90       100       110
EG3IN.PRO    MPTTASWS-YSGSNIRA-NVAYDL-FTAANPNHVTYSGDYELMIW                102
FUSEQIN.PRO  MQSTAEWK-YSGDNLRA-DVAYDL-FTAADPNHETSSGEYELMIW                104
GLIOIN.PRO   INGGADWD-YSGSNIRA-NVAYGI-FTSADPNHVTSSGDYELMIW                103
ACRHYPO.PRO  IQAEWAWTYSGAGDFTT-NVAFDI-FTGETAD                              89
ASPKAWA1.PRO IPTSVTWS-QDDTNVQA-DVSYDL-FTAANADHATSSGDYELMIW                102
ASPACU1.PRO  IPTTARWS-YDNTGIRA-DVAYDL-FTAADINHVTWSGDYELMIW                102
HUMIN.PRO    MRTSVSWT-YDRTDIRA-NVAYDV-FTARDPDHPNWGGDYELMIW                104
11AG8IN.PRO  IGSAPSSVSYRYTGNGVYNAAYDIWLDPTPRTNGVNR--TEIMIW                104
ERWCARIN.PRO NKSITSNVTYSIKATGTYNAAYDIWFHTTDKANWDSSPTDELMIW                110
GLIO314.PRO  ISSGADWD-YTGSNLRA-NAAYDI-FTSANPNHATSSGDYELMIW                103
GLIO3HYP.PRO IPSKWEWRSYTGTDIVA-NVAYDL-FSNTDCGDTP---EYELMIW                100
HGRIS.PRO    MRTSVSWT-YDRTDIRA-NVAYDV-FTARDPDHPNWGGDYEFMIW                104
RHMARIN.PRO  RRAHELDVT-PI-TTGRWNAAYDIWFSPVTNSGNGYSGGAELMIW                105
SLIVIN.PRO   VSAAPSSISYGFVDGAVYNASYDIWLDPTARTDGVNQ--TEIMIW                104
PENNOT.PRO   IPSSVKWN-YDNTDIRA-DVAYDL-FTAADINHDTSSGDYE                     96
PHANHYPO.PRO IPSKWQWESYTGSNVIA-NVAYDL-FSNSDCG                              87
F42HYPO.PRO  IDSTWKWKSYSGSNIVA-DVAYDM-FLSTSPGGDH---NY                      84
EMDESHYP.PRO IPTSWKWQ-YSTTDIVA-NVAYDL-FTSSSAGGDS---EYEFMIW                100
MYCINS.PRO   ----------------A-NVAYDL-FTAADPNHATSSGDYELMIW                 27
CHBRAS.PRO   MQTSVSWE-YNTTDIQA-NVAYDI-FTAEDPDHEHSSGDYELMIW                104
```

FIGURE 3

DNA Sequence of EGIII Without Introns

ATGAAGTTCCTTCAAGTCCTCCCTGCCCTCATACCGGCCGCCCTGGCCCAAACCAGCTGTGA
CCAGTGGGCAACCTTCACTGGCAACGGCTACACAGTCAGCAACAACCTTTGGGGAGCATCAG
CCGGCTCTGGATTTGGCTGCGTGACGGCGGTATCGCTCAGCGGCGGGGCCTCCTGGCACGCA
GACTGGCAGTGGTCCGGCGGCCAGAACAACGTCAAGTCGTACCAGAACTCTCAGATTGCCAT
TCCCCAGAAGAGGACCGTCAACAGCATCAGCAGCATGCCCACCACTGCCAGCTGGAGCTACA
GCGGGAGCAACATCCGCGCTAATGTTGCGTATGACTTGTTCACCGCAGCCAACCCGAATCAT
GTCACGTACTCGGGAGACTACGAACTCATGATCTGGCTTGGCAAATACGGCGATATTGGGCC
GATTGGGTCCTCACAGGGAACAGTCAACGTCGGTGGCCAGAGCTGGACGCTCTACTATGGCT
ACAACGGAGCCATGCAAGTCTATTCCTTTGTGGCCCAGACCAACACTACCAACTACAGCGGA
GATGTCAAGAACTTCTTCAATTATCTCCGAGACAATAAAGGATACAACGCTGCAGGCCAATA
TGTTCTTAGCTACCAATTTGGTACCGAGCCCTTCACGGGCAGTGGAACTCTGAACGTCGCAT
CCTGGACCGCATCTATCAAC

```
                              1                                                            60
               T._reesei      M.........KF.LQVLPALIPAALAQTS...............CDQWATFTGNG..YTV
         H._schweinitzii      M.........KF.LQVLPAILPAALAQTS...............CDQYATFSGNG..YIV
            A._aculeatus__    M.........KAFHL.LAALAGAAVAQQAQ..............LCDQYATYTGGV..YTI
              A._kawachii__   M.........KLSMT.LSLFAATAMGQT................MCSQYDSASSPP..YSV
            A._kawachii_2     M.........KAFHL.LAALSGAAVAQQAQ..............LCDQYATYTGGV..YTI
              A._oryzae__     M.........KLSLA.LATLVATAFSQE................LCAQYDSASSPP..YSV
               H._grisei      M........LKSALLLGAAAVSVQSASIPTIPANLEPRQIR.SLCELYGYWSGNG..YEL
              H._insolens     M........LKSALLLGPAAVSVQSASIPTIPANLEPRQIR.SLCELYGYWSGNG..YEL
   Chaetomium_brasiliense     M........KLTLVLFVSSLA......AATPLGWRERQQQVSLCGQSSSWSGNG..YQL
               F._equseti     M........KSTLLLAGAFAPLAFAKD.................LCEQYGYLSSDG..YSL
            F._javanicum_1    M........KSAIVA.ALAGLAAASPTRLIPRGQ........FCGQWDSETAGA..YTI
            F._javanicum_2    M........K..FFGVVSASLAATAVATPTTPTETIEKRDTTWCDAFGSLATSG..YTV
              G._roseum____1  M........KANIVILSLFAPLAAVAQT................LCGQYSSNTQGG..YIF
              G._roseum____2  M........KSIISFFGLATLVAAAPSQNPTRTQPLEKRATTLCGQWDSVETGG..YTI
              G._roseum____3  M........KFQLLSLTAFAPLSLAA..................LCGQYQSQSQGG..YIF
              G._roseum____4  M........KTGIAYLAAVLPLA.MAES................LCDQYAYLSRDG..YNF
      Memnoniella_echinata    M........KVAAL.LVALSPLAF.AQS................LCDQYSYYSSNG..YEF
      Emericella_desertoru    M.·........K..LLALSLVSLASAASAASIL.SNTFTRRSD.FCGQWDTATVGN..FIV
         Actinomycete_11AG8   MRS......HPRS..ATM.TVLVVLASLGALLTAAAPAQANQQICDRYGTTTIQD.RYVV
           S._lividans_CelB__ MRTLRPQARAPRGLLAALGAVLAAFALVSSLVTAAAPAQADTTICEPFGTTTIQG.RYVV
       Rhodothermus_marinus__ MNVMR..AVLVLSLLLLFGCDWL.FPDGDNGKEPEPEPEPTVELCGRWDARDVAGGRYRV
           Erwinia_carot___   MQTVNTQPHRIFRVLLPAVFSSLLLSSLTVSAASSSNDADKLYF.........GNNKYYL 61                                                           120
               T._reesei      SNNLWGASAGSGF..GCV.TAVSLSGG..ASWHADWQWSGGQNNVKSYQNS..........
         H._schweinitzii      SNNLWGASAGSGF..GCV.TSVSLNGA..ASWHADWQWSGGQNNVKSYQNV..........
            A._aculeatus__    NNNLWGKDAGSG..SQCTTVNSASSAG.TSWSTKWNWSGGGENSVKSYANS..........
              A._kawachii__   NQNLWGEYQGTG..SQCVYVDKLSSSG.ASWHTKWTWSGGGEGTVKSYSNS..........
            A._kawachii_2     NNNLWGKDAGSG..SQCTTVNSASSAG.TSWSTKWNWSGGENSVKSYANS...........
              A._oryzae__     NNNLWGQDSGTGFTSQCVYVDNLSSSG.AAWHTTWTWNGGEGSVKSYSNS....-.....
               H._grisei      LNNLWGKDTATS.GWQCTYLDGTNNGG.IQWNTAWEWQGAPDNVKNYPYV...........
              H._insolens     LNNLWGKDTATS.GWQCTYLDGTNNGG.IQWSTAWEWQGAPDNVKSYPYV.·..........
   Chaetomium_brasiliense     NNNLWGQSRATS.SQCTYLDSSSNSG.IHWHTTWTWEGGEGSVKSYAYS...........
               F._equseti     NNNVWGKDSGTGD..QCTHVNWNNANG.AGWDVEWNWSGGKDNVKSYPNS..........
            F._javanicum_1    YNNLWGKDNAES.GEQCTTNSGEQSDGSIAWSVEWSWTGGQGQVKSYPNA..........
            F._javanicum_2    YHNNWGKGDATS.GSQCTTFTSVSNNNFV.WSTSWTWAGGAGKVKSYSNV..........
              G._roseum____1  NNNMWGMGSGSGS..QCTYVDKVWAEG.VAWHTDWSWSGGDNNVKSYPYS..........
              G._roseum____2  YNNLWGQDNG.S.GSQCLTVEGV.TDGLAAWSSTWSWSGGSSSVKSYSNA...........
              G._roseum____3  NNNKWGQSGSGS..QCLTIDKTWDSN.VAFHADWSWSGGTNNVKSYPNA..........
              G._roseum____4  NNNEWGAATGTGD..QCTVVDSTSSGG.VSWHSDWTWSGSESEIKSYPYS..........
      Memnoniella_echinata    NNNMWGRNSGQGN..QCTYVDYSSPNG.VGWRVNWNWSGGDNNVKSYPYS..........
      Emericella_desertoru    YNNLWGQDNADS.GSQ..TGVDSANGNSISWHTTWSWSGGSSSVKSYANA..........
         Actinomycete_11AG8   QNNRWGTSAT.....QCINVT..GNGFEITQADGS..VPTNGAPKSYPSVYDGCHYG...
           S._lividans_CelB__ QNNRWGSTAP.....QCVTAT..DTGFRVTQADGS..APTNGAPKSYPSVFNGCHYT...
       Rhodothermus_marinus__ INNVWGAETA.....QCIEVGLETGNFTITRADHD..NGNNVA..AYPAIYFGCHWAPAR
           Erwinia_carot___   FNNVWGKDEIKGWQQTIFYNSPISMG....WN..WHWPSSTHSVKAYPSLVSGWHWTAG.

121                                                          180
               T._reesei      .QIAIP.QKRTVNSISSMPTTASW...SYSGSNIRANVAYDL.FTAANPNHVTYSGDYEL
         H._schweinitzii      .QINIP.QKRTVNSIGSMPTTASW...SYSGSDIRANVAYDL.FTAANPNHVTYSGDYEL
            A._aculeatus__    .GLTF..NKKLVSQISQIPTTARW.S...YDNTGIRADVAYDL.FTAADINHVTWSGDYEL
              A._kawachii__   .GLTF..DKKLVSDVSSIPTSVTW.SQD..DTNVQADVSYDL.FTAANADHATSSGDYEL
            A._kawachii_2     .GLSF..NKKLVSQISHIPTAARW.S...YDNTCIRRGRAYDL.FTAADINHVTWSGDYEL
              A._oryzae__     .AVTF..DKKLVSDVQSIPTDVEW.SQDFTNTNVNADVAYDL.FTAADQNHVTYSGDYEL
               H._grisei      .GKQIQRGRK.ISDINSMRTSVSW...TYDRTDLRANVAYDV.FTARDPDHPNWGGDYEL
              H._insolens     .GKQIQRGRK.ISDINSMRTSVSW...TYDRTDIRANVAYDV.FTARDPDHPNWGGDYEL
   Chaetomium_brasiliense     .GRQVSTGLT.IASISDMQTSVSW...EYNTTDIQANVAYDI.FTAEDPDHEHSSGDYEL
               F._equseti     .ALLIGEDKKTISSITNMQSTAEW...KYSGDNLRADVAYDL.FTAADPNHETSSGEYEL
            F._javanicum_1    .VVEI..EKKTLGEVSSIPSA..W.DWTYTGNGIIANVAYDL.FTSSTESGDA...EYEF
            F._javanicum_2    .ALEK..INKKISDIKSVSTR..W.IWRYTGTKMIANVSYDL.WFAPTASSNN...AYEI
              G._roseum____1  .GRELGT.KRIVSSIKSISSGADW...DYTGSNLRANAAYDI.FTSANPNHATSSGDYEV
              G._roseum____2  .VLSA..EAARISAISSIPSK..W.EWSYTGTDIVANVAYDL.FSNTDCGDTP...EYEI
              G._roseum____3  .GLEFSR.GKKVSSIGTINGGADW...DYSGSNIRANVAYGI.FTSADPNHVTSSGDYEL
              G._roseum____4  .GLDLPE..KKIVTSIGSISTGAEW...SYSGSDIRADVAYDT.FTAADPNHATSSGDYEV
      Memnoniella_echinata    .GRQLPT.KRIVSWIGSLPTTVSW...NYQGNNLRANVAYDL.FTAANPNHPNSSGDYEL
      Emericella_desertoru    .AYQF..TSTKLNSLSSIPTS..W.KWQYSTTDIVANVAYDL.FTSSSAGGDS...EYEI
         Actinomycete_11AG8   ...NCAPRTTLPMRISSIGSAPSSVSYRYTGNGVY.NAAYDIWLDPTPRTNGVNR..TEI
           S._lividans_CelB__ ...NCSPGTDLPVRLDTVSAAPSSISYGFVDGAVY.NASYDIWLDPTARTDGVNQ..TEI
       Rhodothermus_marinus__ AIRDCAARAGAVRRAHELDVTP........ITTGRW.NAAYDIWFSPVTNSGNGYSGGAEL
           Erwinia_carot___   ....YTENSGLPIQLSSNKSITSNVTYSIKATGTY.NAAYDIWFHTTDKANWDSSPTDEL 181                                                          240
               T._reesei      MIWLGKYGDIGPIGSS....QGTVNVGGQSWTLYYGYNGAMQV......YSFVAQT.NTT
         H._schweinitzii      MIWLGKYGDIGPIGSS....QGTVNVGGQTWTLYYGYNGAMQV......YSFVAQS.NTT
            A._aculeatus__    MIWLARYGGVQPIGSQ....IATATVDGQTWELWYG......ANGSQKTYSFVAPT.PIT
              A._kawachii__   MIWLARYGSVQPIGKQ....IATATVGGKSWEVW..YGTSTQAGAEQKTYSFVAGS.PIN
            A._kawachii_2     MIWLARYGGVQPLGSQ....IATATVEGQTWELWYG......VNGAQKTYSFVAAN.PIT
```

```
                            A._oryzae__    MIWLARYGTIQPIGTQ....IDTATVEGHTWELWFTY⌣.TIQAGAEQKTYSFVSAT.PIN
                             H._grisei     MIWLARYGGIYPIGTF....HSQVNLAGRTWDLWTGYNGNMRV......YSFLPPSGDIR
                           H._insolens__   MIWLARYGGIYPIGTF....HSQVNLAGRTWDLWTGYNGNMRV......YSFLPPSGDIR
                   Chaetomium_brasiliense  MIWLARYNNVSPIGSS....VATATVGGDTWDLFAGANGDMEV......YSFVAENT.MN
                             F._equseti    MVWLARIGGVQPIGSL....QTSVTIEGHTWELWVGMNGSMKV......FSFVAPT.PVN
                           F._javanicum_1  MIWLSALGGAGPISNDGSP.VATAELAGTSWKL⌊QGKNNQMTV......FSFVAESDV.N
                           F._javanicum_2  MIWVGAYGGALPISTPGKGVIDRPTLAGIPWDVYKGPNGDVTV......ISFVASSNQ.G
                            G._roseum____1 MIWLANLGGLTPIGSP....IGTVKAAGRDWELWDGYNGAMRV......YSFVAPS.QLN
                            G._roseum____2 MIWLSALGGAGPISSTGSS.IATVTIAGASWNLWQGQNNQMAV......FSFVAESDQ.K
                            G._roseum____3 MIWLGKLGDIYPIGNS....IGRVEAANREWDFLVGYNGAMKV......FSFVAPS.PVT
                            G._roseum____4 MIWLANLGGLTPIGSP....IGTVKAAGRDWELWDGYNGAMRV......YSFVAPS.QLN
                      Memnoniella_echinata MIWLGRLGNVYPIGNQ....VATVNIAGQQWNLYYGYNGAMQV......YSFVSPN.QLN
                       Emericella_desertoru MIWLAALGGAGPISSTGSS.IATVTLGGVTWSLYSGPNGSMQV......YSFVASSTT.E
                       Actinomycete_11AG8  MIWFNRVGPVQPIGSP....VGTAHVGGRSWEVWTGSNGSNDVI......SFLAPSA.IS
                        S._lividans_CelB__ MIWFNRVGPIQPIGSP....VGTASVGGRTWEVWSGGNGSNDVL......SFVAPSA.IS
                       Rhodothermus_marinus__ MIWLNWNGGVMPGGSR....VATVELAGATWEVWYADWDWNYIA......YRRTTPT.TS
                        Erwinia_carot___   MIWLNDTNA.....GPAGDYIETVFLGDSSWNVFKGWINADN.GGGWNVFSFVHTSGTNS 241                                                       300
                             T._reesei     NYSGDVKNFFNYLRDNKGYNAAGQYV..LSYQFGTEPF..TGSGT.LNVASWTASI.N..
                         H._schweinitzii   SYSGDVKNFFNYLRDNKGYNAGGQYV..LSYQFGTEPF..TGSGT.LNVASWTASI.N..
                           A._aculeatus__  SFQGDVNDFFKYLTQNHGFPASSQYLI..TLQFGTEPF..TGGPATLSVSNWSASVQQAG
                            A._kawachii__ SWSGDIKDFFNYLTQNQGFPASSQHLI..TLQCGTEPF..TGGPATFTVDNWTASVN...
                           A._kawachii_2  SFQGDINDFFKYLTQNHGFPASSQYLIILALQFGTEPF..TGGPATLNVADWSASVQ...
                             A._oryzae__   TFGGDIKKFFFDYITSKHSFPASAQYLI..NMQFGTEPFFTTGGPVTFTVPNWTASVN..
                             H._grisei    DFSCDIKFFNYLERNHGYPAREQNLIV..YQVGTECF..TGGPARFTCRDFRADL....
                           H._insolens__  DFSCDIKFFNYLERNHGYPAREQNLIV..YQVGTECF..TGGPARFTCRDFRADL....
                   Chaetomium_brasiliense SFSGDVKDFFFDYLEQNVGFPVDDQYLLV..FELGSEAF..TGGPATLSVSQFSANI...
                             F._equseti   NFNADIKQFWDYLTKSQNFPADNQYL..LTFQFGTEPF..TGDNAKFTVTNFNAHLK...
                           F._javanicum_1 NFCGDLADFTDYLVDNHGVSSSQ...ILQSVGAGTEPF..EGTNAVFTTNNYHADVE...
                           F._javanicum_2 NFQADLKEFLNYLTSKQGLPSNY...VATSFQAGTEPF..EGTNAVLKTSAYTISVN...
                            G._roseum____1 SFDGEIMDFFYVVKDMRGFPADSQHL..LTVQFGTEPI..SGSGAKFSVSHWSAKLG...
                            G._roseum____2 SFSGDLNDFIQYLVDSQGYSGSQ...CLYSIGAGTEPF..TGTDAEFITTGYSVSVSAGD
                            G._roseum____3 LFDGNIMDFFYVMRDMQGYPMDKQYL..LSLQFGTEPF..TGSNANFSCWYFGAKIK...
                            G._roseum____4 SFDGEIMDFFYVVKDMRGFPADSQHL..LTVQFGTEPI..SGSGAKFSVSHWSAKLG...
                      Memnoniella_echinata YFSGNVKDFFTYLQYNRAYPADSQYL..ITYQFGTEPF..TGQNAVFTVSNWSAQQNN..
                       Emericella_desertoru SFSADLMDFINYLAENQGLSSSQ...YLTHVQAGTEPF..TGTDATLTVSSYSVSVS...
                       Actinomycete_11AG8  SWSFDVKDFVD.QAVSHGLATPDWYLT..SIQAGFEPW...EGGTGLAVNSFSSAVNAG.
                        S._lividans_CelB__ GWSFDVMDFVR.ATVARGLAENDWYLT..SVQAGFEPW...QNGAGLAVNSFSSTVETGT
                       Rhodothermus_marinus__ VSELDLKAFID.DAVARGYIRPEWYLH..AVETGFELW...EGGAGLRTADFSVTVQ...
                        Erwinia_carot___   A.SLNIRHFTDYLVQTKQWMSDEKYIS..SVEFGTEIF...GGDGQIDITEWRVDVK...

301                                                       360
                             T._reesei     ............................................................
                         H._schweinitzii  ............................................................
                           A._aculeatus__ F..........................................EPWQNGAGLAVNSF....
                            A._kawachii__ ............................................................
                           A._kawachii_2  ............................................................
                             A._oryzae__  ............................................................
                             H._grisei    ...........................................W................
                           H._insolens__  ...........................................W................
                   Chaetomium_brasiliense ...........................................A................
                             F._equseti   ............................................................
                           F._javanicum_1 ............................................................
                           F._javanicum_2 ............................................................
                            G._roseum____1 ............................................................
                            G._roseum____2 SGCDETTTSSQAQSSTVETSTATQPQS...SSTVVPTVTLS.QPSNESTTTPVQSQ....
                            G._roseum____3 ............................................................
                            G._roseum____4 ............................................................
                      Memnoniella_echinata ............................................................
                       Emericella_desertoru ............................................................
                       Actinomycete_11AG8 ..GGNGGTPGTPAACQVSYSTHTWPGGFTVDTTITNTGSTPVDGWELDFTLPAGHTVTSA
                        S._lividans_CelB__ PGGTDPGDPGGPSACAVSYGTNVWQDGFTADVTVTNTGTAPVDGWQLAFTLPSGQRITNA
                       Rhodothermus_marinus__ ............................................................
                        Erwinia_carot___  ............................................................

361
419
                             T._reesei     ..................................
                         H._schweinitzii  ..................................
                           A._aculeatus__ ......SSTV........................
                            A._kawachii__ ..................................
                           A._kawachii_2  ..................................
                             A._oryzae__  ..................................
                             H._grisei    ..................................
                           H._insolens__  ..................................
                   Chaetomium_brasiliense ..................................
                             F._equseti   ..................................
                           F._javanicum_1 ..................................
                           F._javanicum_2 .................................Y
                            G._roseum____1 ..................................
                            G._roseum____2 ......PSSVETTPTAQPQSSSVQTTTTAQA....QPTSGTGCSRRRKRR......AVV
                            G._roseum____3 ..................................
```

Fig 6 (continued)

```
         G._roseum      ..........................................  .................
Memnoniella_echinata   ..........................................  .................
 Emericella_desertoru  ..........................................  .................
    Actinomycete_11AG8 WNALISPASGAVTARSTGSNGRIAANGGTQSFGFQGTSSGTGFNAPAGGRLNGTSCTVR
    S._lividans_CelB   WNASLTPSSGSVTATGASHNARIAP.GGSLSFGFQGTYGGA.FAEPTGFRLNGTACTTV
  Rhodothermus_marinus ..........................................  .................
       Erwinia_carot   ..........................................  .................
```

EGIII-LIKE ENZYMES, DNA ENCODING SUCH ENZYMES AND METHODS FOR PRODUCING SUCH ENZYMES

This is a continuation of application Ser. No. 09/284,327, filed Apr. 10, 1999 now abandoned.

BACKGROUND OF THE INVENTION

1. Field of the Invention

The present invention is directed to novel cellulase compositions which share unique highly conserved regions with a known useful cellulase. More specifically, the present invention relates to a series of newly discovered enzymes from fungi and bacteria which are related by virtue of having at least one of five important conserved amino acid sequences which are also present in EGIII.

2. State of the Art

Cellulases are enzymes which are capable of hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al., (1987), *TIBTECH* 5, 255-261); and are known to be produced by a large number of bacteria, yeasts and fungi.

Primary among the applications that have been developed for the use of cellulolytic enzymes are those involving degrading (wood) cellulose pulp into sugars for (bio)ethanol production, textile treatments like 'stone washing' and 'biopolishing', and in detergent compositions. Thus, cellulases are known to be useful in the treatment of mechanical pulp (see e.g., PCT Publication No. WO 92/16687). Additionally, cellulases are known to be useful as a feed additive (see e.g., PCT Publication No. WO 91/04673) and in grain wet milling.

Of primary importance, however, cellulases are used in the treatment of textiles, i.e., in detergent compositions for assisting in the removal of dirt or grayish cast (see e.g., Great Britain Application Nos. 2,075,028, 2,095,275 and 2,094,826 which illustrate improved cleaning performance when detergents incorporate cellulase) or in the treatment of textiles prior to sale to improve the feel and appearance of the textile. Thus, Great Britain Application No. 1,358,599 illustrates the use of cellulase in detergents to reduce the harshness of cotton containing fabrics and cellulases are used in the treatment of textiles to recondition used fabrics by making their colors more vibrant (see e.g., The Shizuoka Prefectural Hammamatsu Textile Industrial Research Institute Report, Vol. 24, pp. 54-61 (1986)). For example, repeated washing of cotton containing fabrics results in a grayish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Thus, cellulases have been shown to be effective in many industrial processes. Accordingly, there has been a trend in the field to search for specific cellulase compositions or components which have particularly effective performance profiles with respect to one or more specific applications. In this light, cellulases produced (expressed) in fungi and bacteria have been subject of attention. For example, cellulase produced by certain fungi such as *Trichoderma* spp. (especially *Trichoderma longibrachiatum*) have been given much attention because a complete cellulase system capable of degrading crystalline forms of cellulose is readily produced in large quantities via fermentation procedures. This specific cellulase complex has been extensively analyzed to determine the nature of its specific components and the ability of those components to perform in industrial processes. For example, Wood et al., "Methods in Enzymology", 160, 25, pages 234 et seq. (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and β-glucosidases (EC 3.2.1.21) ("BG"). The fungal cellulase classifications of CBH, EG and BG can be further expanded to include multiple components within each classification. U.S. Pat. No. 5,475,101 (Ward et al.) discloses the purification and molecular cloning of one particularly useful enzyme called EGIII which is derived from *Trichoderma longibrachiatum*.

PCT Publication No. WO 94/14953 discloses endoglucanases which are encoded by a nucleic acid which comprises any one of a series of DNA sequences, each having 20 nucleotides.

Ooi et al., *Curr. Genet.*, Vol. 18, pp. 217-222 (1990) disclose the cDNA sequence coding for endoglucanase F1-CMC produced by *Aspergillus aculeatus* which contains the amino acid strings NNLWG (SEQ ID NO: 1), ELMIW (SEQ ID NO: 66) and GTEPFT (SEQ ID NO: 3). Sakamoto et al., *Curr. Genet.*, Vol. 27, pp. 435-439 (1995) discloses the cCNA sequence encoding the endoglucanase CMCase-1 From *Aspergillus kawachii* IFO 4308 which contains the amino acid strings ELMIW (SEQ ID NO: 66) and GTEPFT (SEQ ID NO: 3). Ward et al., discloses the sequence of EGIII having the amino acid strings NNLWG (SEQ ID NO: 1), ELMIW (SEQ ID NO: 66) and GTEPFT (SEQ ID NO: 3). Additionally, two cellulase sequences, one from *Erwinia carotovara* and *Rhodothermus marinus* are disclosed in Saarilahti et al., *Gene*, Vol. 90, pp. 9-14 (1990) and Hreggvidsson et al., *Appl. Environ. Microb.*, Vol. 62, No. 8, pp. 3047-3049 (1996) which contain the amino acid string ELMIW (SEQ ID NO: 66). However, none of these references discloses or suggests that these amino acid strings have any particular relevance in identifying or isolating other cellulases, and particularly fail to suggest that such cellulases are obtainable from such diverse organisms as bacteria, Actinomycetes and other filamentous fungi.

Despite knowledge in the art related to many cellulase compositions having applications in some or all of the above areas, there is a continued need for new cellulase compositions having improved characteristics which are useful in, for example, treating textiles, as a component of detergent compositions, in the treatment of pulp and paper, food processing, and in the conversion of biomass. Thus, while there has been significant improvement in terms of the understanding of cellulase compositions and their activities, there remains a need for alternative cellulase compositions which retain the beneficial effects of known cellulase compositions. In response to this need, Applicants herein surprisingly discovered that novel microbial enzymes which are related to an enzyme known to be useful in industrial applications, i.e., EGIII, can be detected and obtained by virtue of the presence of unique conserved sequences therein.

SUMMARY OF THE INVENTION

The present invention was the product of intensive research by the inventors hereof related to determining whether valuable enzymes could be detected by using a routine PCR techniques based on important and newly discovered conserved sequences found within the sequence of EGIII. Surprisingly, the inventors hereof discovered that these conserved sequences are found not only in EGIII, but also in enzymes derived from organisms from classifications as diverse as filamentous fungi, bacteria and Actinomycete. By utilizing the present invention, Applicants have isolated a number of genes encoding novel cellulases which are related to EGIII in that they possess the conserved regions described herein.

It is an object of the invention to provide novel cellulase compositions which have useful properties when utilized in industrial processes such as textile treatment, laundering of textiles, feed additive technology, baking and food processing, grain wet milling and biomass conversion.

It is another object of the invention to provide evidence for an extensive classification of industrially useful cellulases which are related in structure and function to EGIII.

It is yet another object of the invention to provide for analogs to EGIII which may have additional improved properties in, for example, specific activity, performance in textile treatment, substrate specificity, thermostability, oxidative resistance and alkaline performance profile.

According to the present invention, an enzyme having cellulolytic activity is provided comprising an amino acid sequence comprising therein an amino acid string selected from the group consisting of:

```
(a) Asn-Asn-(Leu/Phe/Lys/Ile)-Trp-     (SEQ ID NO: 1)
    Gly (b) Glu-(Leu/Phe/Ile)-Met-Ile-Trp      (SEQ ID NO: 2)

(c) Gly-Thr-Glu-Pro-Phe-Thr;           (SEQ ID NO: 3)

(d) (Ser/Tyr/Cys/Trp/Thr/Asn/Lys/      (SEQ ID NO: 42)
    Arg)-(Val/Pro)-(Lys/Ala)-(Ser/
    Ala)-(Tyr/Phe);

(e) Lys-Asn-Phe-Phe-Asn-Tyr.           (SEQ ID NO: 5)
```

In a preferred embodiment of the present invention the enzyme is an endoglucanase. Also preferably, the enzyme is derived from a fungal or bacterial source, most preferably from a filamentous fungus.

In another embodiment of the present invention, a DNA encoding the enzyme according to the invention is provided. Also provided are expression vectors comprising that DNA, host cells transformed with such expression vectors and enzymes produced by such host cells.

In yet another embodiment of the present invention, a method of detecting an EGIII-like enzyme is provided comprising the steps of:

(1) preparing a DNA primer which encodes an amino acid string selected from the group consisting of:

```
(a) Asn-Asn-(Leu/Phe/Lys/Ile)-Trp-     (SEQ ID NO: 1)
    Gly (b) Glu-(Leu/Phe/Ile)-Met-Ile-Trp      (SEQ ID NO: 2)

(c) Gly-Thr-Glu-Pro-Phe-Thr;           (SEQ ID NO: 3)

(d) (Ser/Tyr/Cys/Trp/Thr/Asn/Lys/      (SEQ ID NO: 42)
    Arg)-(Val/Pro)-(Lys/Ala)-(Ser/
    Ala)-(Tyr/Phe);
and (e) Lys-Asn-Phe-Phe-Asn-Tyr.           (SEQ ID NO: 5)
```

(2) preparing genomic DNA from an organism of interest;
(3) mixing the primer according to step (1) with the genomic DNA according to step (2) under conditions appropriate to facilitate identification and isolation of a DNA fragment comprising a gene encoding an EGIII like cellulase.

In a preferred embodiment of this aspect of the invention, the method above is utilized to detect an EGIII like enzyme and comprises labeling said DNA primer and mixing in said step (3) under conditions of standard stringency to permit hybridization of said DNA primer with a complementary sequence within the genomic DNA; and subsequent identification and isolation of the gene corresponding to said complementary sequence from said organism of interest which encodes an EGIII cellulase. In another preferred embodiment of this aspect of the invention, step (3) comprises initiating one or more PCR reactions between said DNA primers and said genomic DNA, and identifying and isolating an appropriate fragment produced during such PCR reaction which corresponds to a gene encoding an EGIII like enzyme.

Also within the scope of the present invention is the use of the EGIII like enzyme in textile treatment, e.g., in laundry detergent or stonewashing compositions, in the reduction of biomass, in the production of feed additives or treatment of feed, in the treatment of wood pulp for the production of paper or pulp based products, and in the treatment of starch during grain wet milling or dry milling to facilitate the production of glucose, high fructose corn syrup and/or alcohol.

An advantage of the present invention is that a repeatable protocol has been discovered which permits rapid and simple isolation of genes encoding valuable cellulase enzymes.

BRIEF DESCRIPTION OF THE DRAWINGS

FIG. 1 illustrates the amino acid sequence of EGIII from *Trichoderma longibrachiatum*. (SEQ ID NO: 7)

FIG. 2 illustrates branches of the fungal phylogenetic tree as interpreted by the NCBI.

FIG. 3 illustrates a comparison (SEQ ID NO: 63) of a 102 residue peptide taken from the sequence of EGIII (SEQ ID NO: 43) with a corresponding peptide from *Fusarium equiseti* [FUSEQIN] (SEQ ID NO: 44); *Gliocladium roseum* [GLIOIN] (SEQ ID NO: 45); *Acremonium brachypenium* [ACRHYPO](hypothetical protein sequence without intron) (SEQ ID NO: 46); *Aspergillus kawachii* [ASPKAWA1] (SEQ ID NO: 47); *Aspergillus aculeatus* [ASPACU1] (SEQ ID NO: 48); *Humicola insolens* [HUMIN] (SEQ ID NO: 49); *Actinomycete (streptomyces)* sp. 11AG8 [11AG8IN] (SEQ ID NO: 50); *Erwinia carotovara* [ERWCARIN] (SEQ ID NO: 51); *Gliocladium roseum* [GLI0314] (SEQ ID NO: 52); *Gliocladium roseum* [GLIOHYP](hypothetical protein sequence without intron) (SEQ ID NO: 53); *Humicola grisea* [HGRIS] (SEQ ID NO: 54); *Rhodothermus marinus* [RHMARIN] (SEQ ID NO: 55); *Streptomyces lividans* [SLIVINS] (SEQ ID NO: 56); *Penicillium notatum* [PENNOT] (SEQ ID NO: 57); *Phanerochaete chrysosporium* [PHANHYPO](hypothetical protein sequence without intron) (SEQ ID NO: 58); *Emericella desertoru* [EMDESHYP](hypothetical protein sequence without intron) (SEQ ID NO: 60); *Chaetomium brasillience and* [CHBRAS] (SEQ ID NO: 62); *Myceliopthora thermophila* [MYCINS] (SEQ ID NO: 61)(only 27 amino acids).

FIG. 5 illustrates the DNA sequence of EGIII from *Trichoderma longibrachiatum* without introns. (SEQ ID NO: 6)

FIG. 6 illustrates an alignment of the full length sequence of 20 EGIII-like cellulases in alignment with EGIII, indicating equivalent residues based on primary sequence modeling, including those derived from *Trichoderma reesei* (SEQ ID NO: 8), *Hypocrea schweinitzii* (SEQ ID NO: 9), *Aspergillus* aculeatus (SEQ ID NO: 10), *Aspergillus kawachii* (1) (SEQ ID NO:11), *Aspergillus kawachii* (2) (SEQ ID NO: 12), *Aspergillus oryzae* (SEQ ID NO: 13), *Humicola grisea* (SEQ ID NO: 14), *Humicola insolens* (SEQ ID NO: 15), *Chaetomium brasilliense* ((SEQ ID NO: 16), *Fusarium equiseti* (SEQ ID NO: 17), *Fusarium javanicum* (1) (SEQ ID NO: 18), *Fusarium javanicum* (2) ((SEQ ID NO: 19), *Gliocladium roseum* (1) (SEQ ID NO: 20), *Gliocladium roseum* (2) (SEQ ID NO:21), *Gliocladium roseum* (3) (SEQ ID NO:22), *Gliocladium roseum* (4) ((SEQ ID NO: 23), *Memnoniella echinata* (SEQ ID NO: 24), *Emericella desertoru* (SEQ ID NO: 25), *Actinomycete* 11*AG*8 (SEQ ID NO: 26), *Streptomyces lividans CelB* (SEQ ID NO: 27), *Rhodothermus marinus* (SEQ ID NO: 28), and *Erwinia carotovara* (SEQ ID NO: 29).

DETAILED DESCRIPTION OF THE INVENTION

Figure 4:
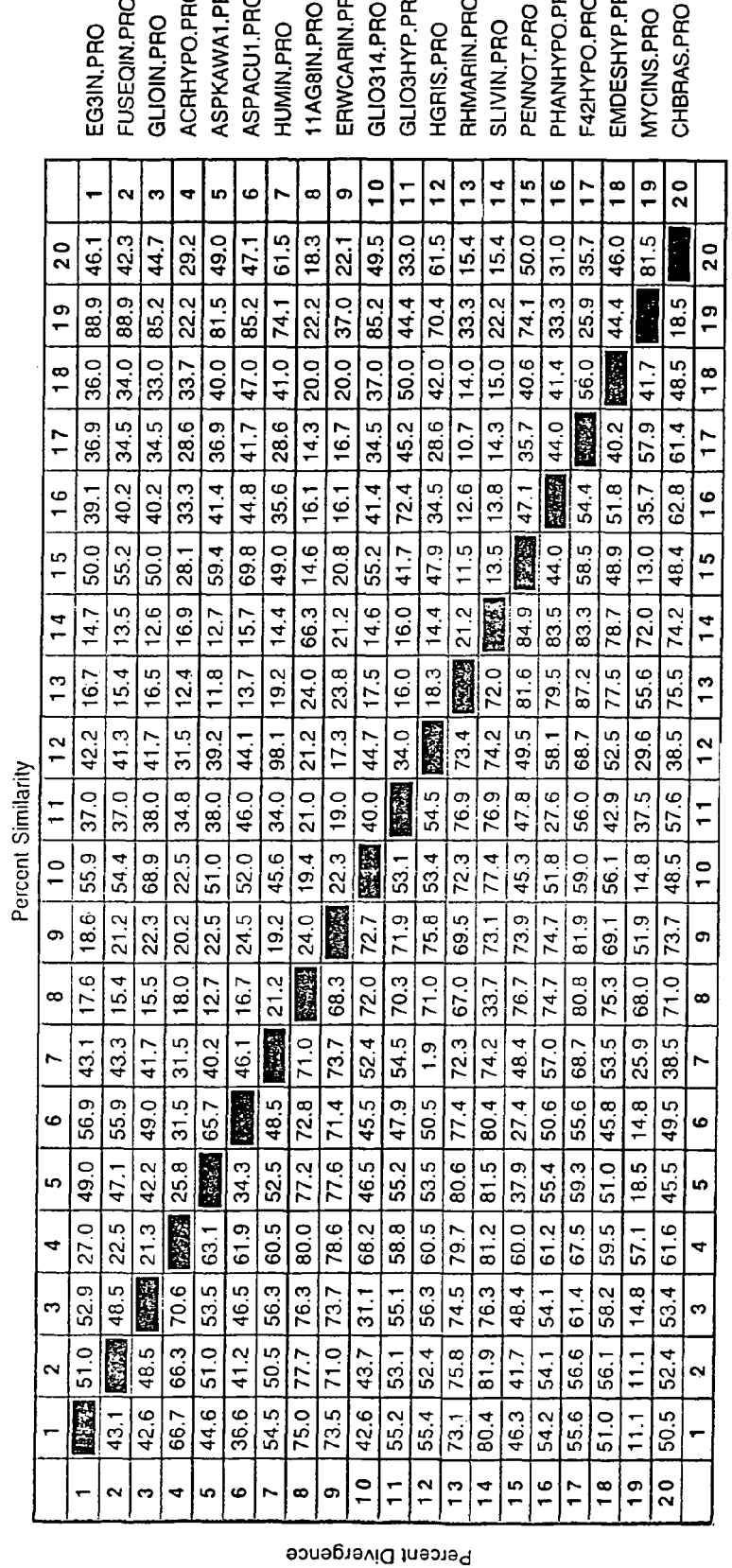
FIG. 4 illustrates a chart showing the percent similarity of protein sequences compared in FIG. 3.

The present invention relates to a purified EGIII like enzyme having cellulolytic activity and which is obtained from organisms other than *Trichoderma* spp., *Humicola* spp., and *Erwinia carotovara* and *Rhodothermus marinus*.

Within the specification, certain terms are disclosed which are defined below so as to clarify the nature of the claimed invention.

"Cellulase" is a well classified category of enzymes in the art and includes enzymes capable of hydrolyzing cellulose polymers to shorter cellooligosaccharide oligomers, cellobiose and/or glucose. Common examples of cellulase enzymes include exo-cellobiohydrolases and endoglucanases and are obtainable from many species of cellulolytic organisms, particularly including fungi and bacteria.

"EGIII" cellulase refers to the endoglucanase component described in Ward et al., U.S. Pat. No.5,475,101 and Proceedings on the SecondTRICEL Symposium on *Trichoderma Reesei* Cellulases And Other Hydrolases, Suominen & Reinikainen eds., Espoo Finland (1993), pp.153-158 (Foundation for Biotechnical and Industrial Fermentation Research, Vol. 8). As discussed therein, EGIII is derived from *Trichoderma reesei (longibrachiatum)* and is characterized by a pH optimum of about 5.8, an isoelectric point (pI) of from about 7.4 and a molecular weight of about 25 kD. The enzyme commonly referred to as EGII from *Trichoderma reesei* has been previously referred to in the literature by the nomenclature EGIII by some authors, but that enzyme differs substantially from the enzyme defined herein as EGIII in terms of molecular weight, pI and pH optimum.

"EG-III like enzyme", "EGIII like protein" or "EGIII like cellulase" according to the present invention means, on the one hand, an enzyme having cellulolytic activity which comprises an amino acid sequence comprising therein an amino acid string selected from the group consisting of one or more of:

```
(a)    Asn-Asn-(Leu/Phe/Lys/Ile)-Trp-Gly (b)    Glu-(Leu/Phe/Ile)-Met-Ile-Trp (c)    Gly-Thr-Glu-Pro-Phe-Thr;

(d)    (Ser/Tyr/Cys/Trp/Thr/Asn/Lys/Arg)-(Val/Pro)-
       (Lys/Ala)-(Ser/Ala)-(Tyr/Phe);
and (e)    Lys-Asn-Phe-Phe-Asn-Tyr.
```

In one embodiment, the enzyme of the invention further has significant structural and/or sequence homology to EGIII. Thus, in one aspect of this embodiment of the invention, the enzyme has at least 30%, preferably at least 40% and most preferably at least 60% amino acid identity to EGIII. However, it should be recognized that homology alone is often not an appropriate measure for whether a particular enzyme identified by the methods described herein represents an EGIII like enzyme. Accordingly, while homologous enzymes are indeed detected by the methods described and exemplified herein, the degree of homology should not be seen as limiting the scope of the invention.

It is contemplated that the EGIII like enzymes of the invention may be found in many organisms which produce cellulases. However, likely sources of EGIII like enzyme include those derived from a bacterial or fungal sources, and more particularly, from an Actinomycete, a Bacillus or a filamentous fungus. In a preferred embodiment, the enzyme is derived from the filamentous fungal family Metazoa, preferably Euascomycetes. Within Metazoa, fungal phylogenetic classifications which produce EGIII like enzymes include the mitosporic Pyrenomycetes (including Acremonium), Sordariales (including Thielavia), Hypocreales (including Nectriaceae such as Fusarium, Necitia, Verticillium, Myrothecium and Gliocladium; and Hypocrea) and Eurotiales (including mitosporic Trichocomaceae such as Aspergillus and Penicillium).

The Euascomycete preferably belongs to Diaporthales, Halosphaeriales, Microascales, Ophiostomatales, Phyllachorales, Sordariales or Xylariales. Also preferably, the Eusacomycete belongs to Hypocreales comprising Clavicipitaceae, Melanosporaceae, Nectriaceae, Niessliaceae or Mitosporic Hypocreales. Further preferably, the Euascomycete belongs to Hypocreaceae, wherein said Hypocreaceae does not comprise Trichoderma. Most preferably, the Euascomycete is *Gliocladium* spp., *Fusarium* spp., *Acremonium* spp., *Myceliophtora* spp., *Verticillium* spp., *Myrothecium* spp., *Penicillium* spp., *Chaetomium* spp., *Emercella* spp., and *Phanerochaete* spp. Specific organisms which are contemplated as possessing EGIII like enzymes include *Chaetomium thermophilum* var. *therm.*, *Chaetomium atrobrunneum*, *Chaetomium brasiliense*, *Chaetomium globosum*, *Chaetomium vitellium*, *Paecilomyces lilacinus*, *Chaetomium thermophilum* var. *dissitum*, *Humicola insolens*, *Humicola brevis*, *Memnoniella echinata*, *Fusarium equiseti*, *Fusarium oxysporum*, *fusarium stilboides*, *Myceliophthora thermophila*, *Fusarium javanicum*, *Humicola grisea* var. *thermoidea*, *Stibella thermophila*, *Melanocarpus albomyces*, *Arthrobotrys superba*, *Myceliophthora hinunilea*, *Chaetomium pachypodiodes*, *Myrothecium verrucaria*, *Penicillium crysogenum*, *Malbranchea sulfurea*, *Lunulospora curvula*, *Emericella desertorum*, *Acremonium strictum*, *Cylindrocarpon heteronema*, and *Ulocladium chartarum*.

Within the Actinomycetes, Streptomyces has been shown to possess EGIII like enzymes. Where the species of origin of the EGIII like cellulase is *Aspergillus*, the specific species is an *Aspergillus* comprising *A. aeneus, A. anthodesmis, A. aureofulgens, A. aureolatus, A. avenaceus, A. awamorii, A. bisporus, A. brunneouniseriatus, A. campestris, A. caesiellus, A. candidus, A. carbonarius, A. carneus, A. cervinus, A. clavatoflavus, A. clavatoanicus, A. clavatus, A. conicus, A. conjunctus, A. crustosus, A. deflectus, A. dimorphicus, A. eburneocremeus, A. egyptiacus, A. ellipticus, A. elongatus, A. ficuum, A. flaschentraegeri, A. flavus, A. fumigatus, A. giganteus, A. glaucus, A. gorakhpurensis, A. gracilis, A. iizuke, A. itaconicus, A. japonicus, A. kambarensis, A. kanagawaensis, A. lanosus, A. leporis, A. longivesica, A. mellinus, A. multicolor, A. niger, A. nomius, A. nutans, A. ochraceus, A. pallidus, A. panamensis, A. parasiticus, A. parvulus, A. penicillioides, A. phialisepticus, A. phoenicis, A. proliferans,*

*A.pulvinus, A.puniceus, A.raperi, A.recurvatus, A.restrictus, A.shirousami, A.sojae, A.sparsus, A. subolivaceus, A.subsessilis, A.tamarii, A.terreus, A.terricola, A. thomii, A.tubingensis, A. unguis, A.unilateralis, A.ustus, A.versicolor, A.wentii, A.xerophilus, A.zonatus*, A.sp.

Another embodiment comprising EGIII like enzymes according to the invention may be obtained according to the following methods. DNA primers are constructed which encode an amino acid sequence selected from the group consisting of one or more of:

(a) Asn-Asn-(Leu/Phe/Lys/Ile)-Trp-Gly (SEQ ID NO: 1)

(b) Glu-(Leu/Phe/Ile)-Met-Ile-Trp (SEQ ID NO: 2)

(c) Gly-Thr-Glu-Pro-Phe-Thr; (SEQ ID NO: 2)

(d) (Ser/Tyr/Cys/Trp/Thr/Asn/Lys/Arg)-(Val/Pro)-(Lys/Ala)-(Ser/Ala)-(Tyr/Phe); (SEQ ID NO: 42)
and (e) Lys-Asn-Phe-Phe-Asn-Tyr. (SEQ ID NO: 5)

and used to obtain DNA, and genes, encoding enzymes having cellulolytic activity according to established methods.

In the preferred embodiment according to this aspect of the invention, degenerate primers are prepared corresponding to one or more of the above peptides. The peptides are combined with a genomic DNA from a target organism (i.e., the organism in which the EGIII like enzyme is sought) under conditions suitable to initiate a standard PCR reaction. In this embodiment, it is advantageous to select degenerate primers corresponding to peptides (a) and/or (d) plus primers corresponding to (c) and/or (e) and perform PCR with those peptides. After the PCR reaction has been performed, the resulting DNA is run on a polyacrylamide gel and bands corresponding in size to the EGIII fragment comprising peptides (a) and/or (d) in addition to (c) and/or (e), i.e., those in the 400-1000 base pair range, are selected out. These fragments are pooled and reamplified using primers corresponding to peptides (a) and/or (d) plus primers corresponding to peptide (b) or, alternatively, using primers corresponding to peptide (c) and/or (e) plus primers corresponding to peptide (b). Strong bands of the expected size (in the case of EGIII like enzymes, the bands will correspond to the approximately 250-500 base pair range) are excised and sequenced. The sequence is then used to design exact match primers and these primers used with the technique referred to as rapid amplification of genomic DNA ends to obtain the full length gene, see e.g., Mizobuchi et al., *BioTechniques*, Vol. 15, No. 2, pp. 215-216 (1993).

However, it is also possible to use the degenerate DNA's as hybridization probes against a genomic library obtained from a target organism to analyze whether a given fragment correlates to a similar sequence in the target organism. A useful hybridization assay is as follows: Genomic DNA from a particular target source is fragmented by digestion with a restriction enzyme(s), e.g., EcoR I, Hind III, Bam HI, Cla I, Kpn I, Mlu I, Spe I, Bgl II, Nco I, Xba I, Xho I and Xma I (supplied by New England Biolabs, Inc., Beverly, Mass. and Boehringer Mannheim) according to the manufacturer's instructions. The samples are then electrophoresed through an agarose gel (such as, for example, 0.7% agarose) so that separation of DNA fragments can be visualized by size. The gel may be briefly rinsed in distilled $H_2O$ and subsequently depurinated in an appropriate solution (such as, for example, 0.25 M HCl) with gentle shaking followed by denaturation for 30 minutes (in, for example, 0.4 M NaOH). A renaturation step may be included in which the gel is placed in 1.5 M NaCl, IM Tris, pH 7.0 with gentle shaking for 30 minutes. The DNA should then be transferred onto an appropriate positively charged membrane, for example the *Maximum Strength Nytran Plus* membrane (Schleicher & Schuell, Keene, N.H.), using a transfer solution (such as, for example, 6× SSC (900 mM NaCl, 90 mM trisodium citrate). After the transfer is complete, generally at about 2 hours or greater, the membrane is rinsed and air dried at room temperature after using a rinse solution (such as, for example, 2× SSC[2× SSC =300 mM NaCl, 30 mM trisodium citrate]). The membrane should then be prehybridized, (for approximately 2 hours or more) in a suitable prehybridization solution (such as, for example, an aqueous solution containing per 100 mls: 30-50 mls formamide, 25 mls of 20× SSPE (1× SSPE=0.18 M NaCl, 1 mM EDTA, 10 mM $NaH_2PO_4$, pH 7.7), 2.5 mls of 20% SDS, 1 ml of 10 mg/ml sheared herring sperm DNA).

A DNA probe corresponding to the peptide sequences above should be isolated by electrophoresis in an agarose gel, the fragment excised from the gel and recovered from the excised agarose. This purified fragment of DNA is then labeled (using, for example, the *Megaprime* labeling system according to the instructions of the manufacturer to incorporate $p^{32}$ in the DNA (Amersham International plc, Buckinghamshire, England)). The labeled probe is denatured by heating to 95° C. for 5 minutes and immediately added to the prehybridization solution above containing the membrane. The hybridization reaction should proceed for an appropriate time and under appropriate conditions, for example, for 18 hours at 37° C. with gentle shaking. The membrane is rinsed (for example, in 2× SSC/0.3% SDS) and then washed with an appropriate wash solution and with gentle agitation. The stringency desired will be a reflection of the conditions under which the membrane (filter) is washed.

Specifically, the stringency of a given reaction (i.e., the degree of homology necessary for successful hybridization) will largely depend on the washing conditions to which the filter from the Southern Blot is subjected after hybridization. "Low-stringency" conditions as defined herein will comprise washing a filter from a Southern Blot with a solution of 0.2× SSC/0.1% SDS at 20° C. for 15 minutes. Standard-stringency conditions comprise a further washing step comprising washing the filter from the Southern Blot a second time with a solution of 0.2× SSC/0.1% SDS at 37° C. for 30 minutes.

The DNA which hybridizes with the DNA primers outlined above and thus identified by this method a corresponding EGIII encoding gene may be isolated by routine methods and used to express the corresponding EGIII like enzyme according to routine techniques. A preferred cloning procedure comprises the rapid amplification of genomic DNA ends described in, e.g., Mizobuchi et al., BioTechniques, Vol. 15, No. 2, pp. 215-216 (1993). Upon obtaining the cloned gene, routine methods for insertion of the DNA into a vector which can then be transformed into a suitable host cell are used. Culturing the transformed host cell under appropriate conditions then results in production of the EGIII like cellulase which can be obtained, purified and prepared as necessary for a particular application.

The EGIII like enzymes of the invention are preferably isolated or purified. In the context of the present invention, purification or isolation generally means that the EGIII like cellulase is altered from its natural state by virtue of separating the EGIII like cellulase from some or all of the naturally occurring substituents with which it is associated in nature, e.g., the source organism or other cellulases or enzymes expressed by the source organism in conjunction with the EGIII cellulase. Similarly, the EGIII like enzymes of the invention may be combined with other components which are not naturally present in the natural state. Isolation of purification may be accomplished by art recognized separation techniques such as ion exchange chromatography, affinity chromatography, hydrophobic separation, dialysis, protease treatment, ammonium sulphate precipitation or other protein salt precipitation techniques, centrifugation, size exclusion chromatography, filtration, microfiltration, gel electrophoresis or separation on a gradient to remove whole cells, cell debris, impurities, extraneous proteins, or enzymes undesired in the final composition.

"Cellulose containing fabric" means any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g. lyocell). Specifically included within the definition of cellulose containing fabric is any yarn or fiber made of such materials. Cellulose containing materials are often incorporated into blends with materials such as synthetic fibers and natural non-cellulosic fibers such as wool and silk.

"Cotton-containing fabric" means sewn or unsewn fabrics, yarns or fibers made of pure cotton or cotton blends including cotton woven fabrics, cotton knits, cotton denims, cotton yarns, raw cotton and the like. When cotton blends are employed, the amount of cotton in the fabric is preferably at least about 35 percent by weight cotton. When employed as blends, the companion material employed in the fabric can include one or more non-cotton fibers including cellulosic or synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Stonewashing composition" means a formulation for use in stonewashing cellulose containing fabrics. Stonewashing compositions are used to modify cellulose containing fabrics prior to presentation for consumer sale, i.e., during the manufacturing process. In contrast, detergent compositions are intended for the cleaning of soiled garments.

"Stonewashing" means the treatment of cellulose containing fabric with a cellulase solution under agitating and cascading conditions, i.e., in a rotary drum washing machine, to impart a "stonewashed" appearance to the denim. The cellulase solution according to the instant invention will functionally replace the use of stones in such art recognized methods, either completely or partially. Methods for imparting a stonewashed appearance to denim are described in U.S. Pat. No. 4,832,864 which is incorporated herein by reference in its entirety. Generally, stonewashing techniques have been applied to indigo dyed cotton denim.

"Detergent composition" means a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers. Such compositions are generally used for cleaning soiled garments and are not used during the manufacturing process, in contrast to stonewashing compositions. Detergent compositions comprising cellulase are described in, for example, Clarkson et al., U.S. Pat. No. 5,290,474 and EP Publication No. 271 004, incorporated herein by reference.

"Derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of an enzyme derivative is preferably achieved by modifying a DNA sequence which encodes for the native protein, transformation of that DNA sequence into a suitable host, and expression of the modified DNA sequence to form the derivative enzyme. The derivative of the invention includes peptides comprising altered amino acid sequences in comparison with a precursor enzyme amino acid sequence (e.g., a wild type or native state enzyme), which peptides retain a characteristic enzyme nature of the precursor enzyme but which have altered properties in some specific aspect. For example, a cellulase derivative may have an increased pH optimum or increased temperature or oxidative stability but will retain its characteristic cellulolytic activity. Similarly, derivatives according to the present invention include a cellulose binding domain portions of which have either been added, removed or modified in such a way so as to significantly impair or enhance its cellulose binding ability. It is contemplated that derivatives according to the present invention may be derived from a DNA fragment encoding a cellulase derivative wherein the functional activity of the expressed cellulase derivative is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained. Derivative further includes chemical modification to change the characteristics of the enzyme.

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control transcription, a sequence encoding suitable ribosome-binding sites on the mRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* (*longibrachiatum*) is cbhI. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2 µplasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook et al., *Molecular Cloning: A Laboratory Manual, Second Edition*, Cold Spring Harbor Press (1989). Often, such expression vectors including the DNA sequences of the invention are transformed into a unicellular host by direct insertion into the genome of a particular species through an integration event (see e.g., Bennett & Lasure, *More Gene Manipulations in Fungi*, Academic Press, San Diego, pp. 70-76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally procaryotic or eucaryotic hosts, including any transformable microorganism in which expression can be achieved. Specifically, host strains may be *Bacillus subtilis, Escherichia coli, Trichoderma reesei (longibrachiatum), Saccharomyces cerevisiae* or *Aspergillus niger.* Host cells are transformed or transfected with vectors constructed using recombinant DNA techniques. Such transformed host cells are capable of both replicating vectors encoding swollenin and its variants (mutants) or expressing the desired peptide product. In a preferred embodiment according to the present invention, "host cell" means both the cells and protoplasts created from the cells of *Trichoderma* sp.

"Signal sequence" means a sequence of amino acids bound to the N-terminal portion of a protein which facilitates the secretion of the mature form of the protein outside of the cell. This definition of a signal sequence is a functional one. The mature form of the extracellular protein lacks the signal sequence which is cleaved off during the secretion process.

"DNA vector" means a nucleotide sequence which comprises one or more DNA fragments or DNA variant fragments encoding an EGIII like enzyme or derivatives described above which can be used, upon transformation into an appropriate host cell, to cause expression of the EGIII like cellulase. &P "Functionally attached to" means that a regulatory region, such as a promoter, terminator, secretion signal or enhancer region is attached to a structural gene and controls the expression of that gene.

The present invention relates to the expression, purification and/or isolation and use of EGIII like enzymes and derivatives of such EGIII like enzyme. These enzymes are preferably prepared by recombinant methods utilizing the gene identified and isolated according to the methods described above. However, enzymes for use in the present invention may be obtained by other art recognized means such as purification from natural isolates.

It is conceived by the inventors that the microorganism to be transformed for the purpose of expressing an EGIII like enzyme according to the present invention may advantageously comprise a strain derived from *Trichoderma* sp. Thus, a preferred mode for preparing EGIII like enzymes according to the present invention comprises transforming a *Trichoderma* sp. host cell with a DNA construct comprising at least a fragment of DNA encoding a portion or all of the EGIII like enzyme detected as described above. The DNA construct will generally be functionally attached to a promoter. The transformed host cell is then grown under conditions so as to express the desired protein. Subsequently, the desired protein product is purified to substantial homogeneity.

However, it may in fact be that the best expression vehicle for a given DNA encoding an EGIII like enzyme may differ. Thus, it may be that it will be most advantageous to express a protein in a transformation host which bears phylogenetic similarity to the source organism for the EGIII like enzyme. Accordingly, the present description of a *Trichoderma* spp. expression system is provided for illustrative purposes only and as one option for expressing the EGIII like enzyme of the invention. One of skill in the art, however, may be inclined to express the DNA encoding EGIII like enzyme in a different host cell if appropriate and it should be understood that the source of the EGIII like enzyme should be considered in determining the optimal expression host. Additionally, the skilled worker in the field will be capable of selecting the best expression system for a particular gene through routine techniques utilizing the tools available in the art.

In one embodiment, the strain comprises *T. reesei (longibrachiatum)* which is a useful strain for obtaining overexpressed protein. For example, RL-P37, described by Sheir-Neiss et al. in *Appl. Microbiol. Biotechnology,* 20 (1984) pp.46-53 is known to secrete elevated amounts of cellulase enzymes. Functional equivalents of RL-P37 include *Trichoderma reesei (longibrachiatum)* strain RUT-C30 (ATCC No. 56765) and strain QM9414 (ATCC No. 26921). It is contemplated that these strains would also be useful in overexpressing EGIII like enzymes.

Where it is desired to obtain the EGIII like cellulase in the absence of potentially detrimental native cellulolytic activity, it is useful to obtain a *Trichoderma* host cell strain which has had one or more cellulase genes deleted prior to introduction of a DNA construct or plasmid containing the DNA fragment encoding the EGIII like enzyme. Such strains may be prepared by the method disclosed in U.S. Pat. No. 5,246,853 and WO 92/06209, which disclosures are hereby incorporated by reference. By expressing an EGIII like enzyme in a host microorganism that is missing one or more cellulase genes, the identification and subsequent purification procedures are simplified. Any gene from *Trichoderma* sp. which has been cloned can be deleted, for example, the cbh1, cbh2, egl1, and egl3 genes as well as those encoding EGIII and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed fungus. Any selectable marker gene which is expressed in the selected microorganism will be suitable. For example, with *Trichoderma* sp., the selectable marker is chosen so that the presence of the selectable marker in the transformants will not significantly affect the properties thereof. Such a selectable marker may be a gene which encodes an assayable product. For example, a functional copy of a *Trichoderma* sp. gene may be used which if lacking in the host strain results in the host strain displaying an auxotrophic phenotype.

In a preferred embodiment, a pyr4 derivative strain of *Trichoderma* sp. is transformed with a functional pyr4 gene, which thus provides a selectable marker for transformation. A pyr4 derivative strain may be obtained by selection of *Trichoderma* sp. strains which are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4 derivative strains which lack a functional orotidine monophosphate decarboxylase enzyme and require uridine for growth by selecting for FOA resistance. Using the FOA selection technique it is also possible to obtain uridine requiring strains which lack a functional orotate pyrophosphoribosyl transferase. It is possible to transform these cells with a functional copy of the gene encoding this enzyme (Berges and Barreau, *Curr. Genet.*, 19, 1991, pp. 359-365). Selection of derivative strains is easily performed using the FOA resistance technique referred to above, and thus, the pyr4 gene is preferably employed as a selectable marker.

To transform pyr4 *Trichoderma* sp. so as to be lacking in the ability to express one or more cellulase genes, a single DNA fragment comprising a disrupted or deleted cellulase gene is then isolated from the deletion plasmid and used to transform an appropriate pyr *Trichoderma* host. Transformants are then identified and selected based on their ability to express the pyr4 gene product and thus compliment the uridine auxotrophy of the host strain. Southern blot analysis is then carried out on the resultant transformants to identify and confirm a double crossover integration event which replaces part or all of the coding region of the genomic copy of the gene to be deleted with the pyr4 selectable markers.

Although the specific plasmid vectors described above relate to preparation of pyr transformants, the present invention is not limited to these vectors. Various genes can be deleted and replaced in the *Trichoderma* sp. strain using the above techniques. In addition, any available selectable markers can be used, as discussed above. In fact, any *Trichoderma* sp. gene which has been cloned, and thus identified, can be deleted from the genome using the above-described strategy.

As stated above, the host strains used are derivatives of *Trichoderma* sp. which lack or have a nonfunctional gene or genes corresponding to the selectable marker chosen. For example, if the selectable marker of pyr4 is chosen, then a specific pyr4 derivative strain is used as a recipient in the transformation procedure. Similarly, selectable markers comprising *Trichoderma* sp. genes equivalent to the *Aspergillus nidulans* genes amdS, argB, trpC, niaD may be used. The corresponding recipient strain must therefore be a derivative strain such as argB, trpC, niaD, respectively.

DNA encoding the EGIII like enzyme is then prepared for insertion into an appropriate microorganism. According to the present invention, DNA encoding a EGIII like enzyme comprises all of the DNA necessary to encode for a protein which has functional cellulolytic activity. The DNA fragment or DNA variant fragment encoding the EGIII like enzyme or derivative may be functionally attached to a fungal promoter sequence, for example, the promoter of the cbh1 or egl1 gene.

It is also contemplated that more than one copy of DNA encoding a EGIII like enzyme may be recombined into the strain to facilitate overexpression. The DNA encoding the EGIII like cellulase may be prepared by the construction of an expression vector carrying the DNA encoding the cellulase. The expression vector carrying the inserted DNA fragment encoding the EGIII like cellulase may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene coding region, and terminator sequence all originate from the gene to be expressed. Gene truncation may be obtained where desired by deleting away undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high level transcription and a selectable marker. It is contemplated that the coding region for a gene or part thereof can be inserted into this general purpose expression vector such that it is under the transcriptional control of the expression cassettes promoter and terminator sequences. For example, pTEX is such a general purpose expression vector. Genes or part thereof can be inserted downstream of the strong cbh1 promoter.

In the vector, the DNA sequence encoding the EGIII like enzyme of the present invention should be operably linked to transcriptional and translational sequences, i.e., a suitable promoter sequence and signal sequence in reading frame to the structural gene.

The promoter may be any DNA sequence which shows transcriptional activity in the host cell and may be derived from genes encoding proteins either homologous or heterologous to the host cell. The signal peptide provides for extracellular production of the EGIII like enzyme or derivatives thereof. The DNA encoding the signal sequence is preferably that which is naturally associated with the gene to be expressed, however the signal sequence from any suitable source, for example an exo-cellobiohydrolase or endoglucanase from *Trichoderma*, is contemplated in the present invention.

The procedures used to ligate the DNA sequences coding for the EGIII like enzyme of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in *Trichoderma* sp. is very low. Accordingly, uptake of the desired DNA sequence, gene or gene fragment is at best minimal. There are a number of methods to increase the permeability of the *Trichoderma* sp. cell wall in the derivative strain (i.e., lacking a functional gene corresponding to the used selectable marker) prior to the transformation process.

The preferred method in the present invention to prepare *Trichoderma* sp. for transformation involves the preparation of protoplasts from fungal mycelium. The mycelium can be obtained from germinated vegetative spores. The mycelium is treated with an enzyme which digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M to 1.2 M. It is preferable to use about a 1.2 M solution of sorbitol in the suspension medium.

Uptake of the DNA into the host *Trichoderma* sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the *Trichoderma* sp. strain and the plasmid DNA is transferred to the nucleus. This fusion frequently leaves multiple copies of the plasmid DNA tenderly integrated into the host chromosome.

Usually a suspension containing the *Trichoderma* sp. protoplasts or cells that have been subjected to a permeability treatment at a density of $10^8$ to $10^9$/ml, preferably $2 \times 10^8$/ml are used in transformation. A volume of 100 microliters of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated at room temperature before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if Pyr⁺ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the EGIII like enzymes or derivatives thereof are recovered in active form from the host cell after growth in liquid media either as a result of the appropriate post translational processing of the novel EGIII like enzyme or derivatives thereof.

The expressed EGIII like enzyme may be recovered from the medium by conventional techniques including separations of the cells from the medium by centrifugation, filtration, and precipitation of the proteins in the supernatant or filtrate with a salt, for example, ammonium sulphate. Additionally, chromatography procedures such as ion exchange chromatography or affinity chromatography may be used. Antibodies (polyclonal or monoclonal) may be raised against the natural purified EGIII like enzyme, or synthetic peptides may be prepared from portions of the EGIII like enzyme molecule and used to raise polyclonal antibodies.

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers. Immature cotton is significantly more amorphous than mature cotton and results in a lesser quality fabric when present due to, for example, uneven dyeing. The composition contemplated in the present invention further includes a cellulase component for use in washing of a soiled manufactured cellulose containing fabric. For example, the cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques for cellulase treatment of textiles are described in, for example, EP Publication No. 220 016 and GB Application Nos. 1,368, 599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

Treating according to the instant invention comprises preparing an aqueous solution which contains an effective amount of cellulase together with other optional ingredients including, for example, a buffer, a surfactant, and/or a scouring agent. An effective amount of cellulase enzyme composition is a concentration of cellulase enzyme sufficient for its intended purpose. Thus, for example, an "effective amount" of cellulase in a stonewashing composition according to the present invention is that amount which will provide the desired effect, e.g., to produce a worn and faded look in the seams and on fabric panels. Similarly, an "effective amount" of cellulase in a composition intended for improving the feel and/or appearance of a cellulose containing fabric is that amount which will produce measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity. The determination of the optimal pH range of the cellulases of the invention can be ascertained according to well known techniques. Suitable buffers at pH within the activity range of the cellulase are well known to those skilled in the art in the field.

In addition to cellulase and a buffer, the treating composition may optionally contain a surfactant. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates will permit facile formulation of the cellulase solutions as well as permit feasible transportation of the composition to the location where it will be used. The treating concentrate can be in any art recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the cellulase composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, i.e., improving the feel and/or appearance of a fabric. The cellulose containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the cellulase enzyme to react efficiently with cellulose containing fabric, in this case to produce the stonewashed effect. However, such conditions are readily ascertainable by one of skill in the art. The reaction conditions effective for the stonewashing compositions of the present invention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., which conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all effect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal, anti-graying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase protecting agent. The granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, non-ionic and ampholytic surfactants well known for their use in detergent compositions.

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; and alkanesul-fonates. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, fatty acid glycerine monoesters, and the like. Suitable surfactants for use in this invention are disclosed in British Patent Application No. 2 094 826 A, the disclosure of which is incorporated herein by reference. Mixtures of such surfactants can also be used. The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. In addition to the cellulase composition and the surfactant(s), the detergent compositions of this invention can optionally contain one or more of the following components:

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic Surfactants and Long-Chain Fatty Acid Salts

Such cationic surfactants and long-chain fatty acid salts include saturated or unsaturated fatty acid salts, alkyl or alkenyl ether carboxylic acid salts, a-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent Sequestering Agents

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or Inorganic Electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Masking Agents for Factors Inhibiting the Cellulase Activity

The cellulase composition of this invention are deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-Activators

The activators may vary depending on the specific cellulase. In the presence of proteins, cobalt and its salts, magnesium and its salts, and calcium and its salts, potassium and its salts, sodium and its salts or monosaccharides such as mannose and xylose, many cellulases are activated and their deterging powers are improved remarkably.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzenesulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose containing fabrics with detergent compositions according to the present invention, will be readily ascertainable by those of skill in the art. Accordingly, the appropriate conditions effective for treatment with the present detergents will correspond to those using similar detergent compositions which include known cellulases.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

It is contemplated that compositions comprising cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 25 87372, respectively.

In order to further illustrate the present invention and advantages thereof, the following specific examples are given with the understanding that they are being offered to illustrate the present invention and should not be construed in any way as limiting its scope.

EXAMPLE

Genomic DNA was prepared for several different microorganisms for the purpose of undertaking a PCR reaction to determine whether EGIII like enzymes are encoded by the DNA for a particular organism.

Genomic DNA is obtained from *Acremonium brachypenium* deposit no. CBS 866.73; *Chaetomium brasillience* deposit no. CBS 140.50; *Chaetomium vitellium* deposit no. CBS 250.85; *Emericella desertoru* deposit no. CBS 653.73; *Fusarium equiseti* deposit no. CBS 185.34; *Gliocladium roseum* deposit no. CBS 443.65; *Humicola grisea* var. *thermoidia* deposit no. CBS 225.63; *Myceliopthora thermophila* deposit no. ATCC 48102-48104; *Penicillium notatum* deposit no. ATCC 9178, 9179; and *Phanerochaete chrysosporium* deposit no. ATCC 28326 and isolated according to standard methods.

PCR was performed on a standard PCR machine such as the PCT-150 MicroCycler from MJ Research Inc. under the following conditions:
1) 1 minute at 98° C. for 1 cycle;
2) 1 minute at 94° C., 90 seconds at 40° C., 1 minute at 72° C.
3) repeat step 2 for 30 cycles
4) 7 minutes at 72° C. for 1 cycle
5) lower temperature to 15° C. for storage and further analysis.

The following DNA primers were constructed for use in amplification of EGIII like genes from the libraries constructed from the various microorganisms. All symbols used herein for protein and DNA sequences correspond to IUPAC IUB Biochemical Nomenclature Commission codes.

```
BOX1:
primers coding for (N/Q)NLWG        (SEQ ID NO: 64)
forward primer FRG001:
AAY AAY YTN TGG GG                  (SEQ ID NO: 30)
forward primer FRG002:
CAR AAY YTN TGG GG                  (SEQ ID NO: 31)

BOX1':
primers coding for NNN(F/L/Y/I/L/   (SEQ ID NO: 65)
N/K)WG
forward primer FRG010:
AAY AAY AAY HWI TGG GG              (SEQ ID NO: 32)

BOX2:
primers coding for ELMIW            (SEQ ID NO: 66)
forward primer FRG003:
GAR YTN ATG ATH TGG                 (SEQ ID NO: 33)
reversed primer FRG004:
CCA DAT CAT NAR YTC                 (SEQ ID NO: 34)

BOX2':
primers coding for YELMIW           (SEQ ID NO: 67)
forward primer FRG011:
TAY GAR YTI ATG ATH TGG             (SEQ ID NO: 35)
reversed primer FRG012:
CCA DAT CAT IAR YTC RTA             (SEQ ID NO: 36)

BOX3:
primers coding for GTE(P/C)FT       (SEQ ID NO: 68)
reversed primer FRG005:
GTR AAN GGY TCR GTR CC              (SEQ ID NO: 37)
reversed primer FRG006:
GTR AAN GGY TCR GTY CC              (SEQ ID NO: 38)
reversed primer FRG007:
GTR AAN GGY TCY GTR CC              (SEQ ID NO: 39)
reversed primer FRG008:
GTR AAN GGY TCY GTY CC              (SEQ ID NO: 40)
reversed primer FRG009:
GTR AAR CAY TCN GTN CC              (SEQ ID NO: 41)
```

PCR conditions for PWO polymerase (Boehringer Mannheim, Cat # 1644-947) comprise a 100 microliter solution made of 10 microliter of 10× reaction buffer (10× reaction buffer comprising 100 mM Tris HCl, pH 8-8.5; 250 mM KCl; 50 mM $(NH_4)_2SO_4$; 20 mM $MgSO_4$); 0.2 mM each of dATP, dTTP, dGTP, dCTP (final concentration), 1 microliter of 100 nanogram/microliter genomic DNA, 1 microliter of PWO at 1 unit per microliter, 500 mM primers (final concentration) and water to 100 microliters. The solution is overlaid with mineral oil.

The PCR strategy was as follows: forward primers for BOX1 and BOX1' were combined with reversed primers from BOX3 in a mixture with the desired genomic DNA sample and run on a gel to obtain fragments in the 400-1000 base pair range. The obtained fragments were then pooled and the pool split into two approximately equal portions. The first pool was combined with the forward primers from BOX1 and BOX1' along with the reversed primer from BOX2. The second pool was combined with the forward primer from BOX2 along with the reversed primers from BOX3. Fragments having the approximate size relative to an EGIII like cellulase considering the location of the primers within the gene, in this case corresponding to those between 250-500 base pairs, were isolated and sequenced. Partial sequences for EGIII like cellulase genes are provided in FIG. 3 (SEQ ID NOs: 43-62).

The isolated and partially sequenced DNA and the corresponding amino acid sequences (of approximately 100 residues) were analyzed to determine their relationship to EGIII. The results of this sequence alignment are shown in FIG. 3 (SEQ ID NOs: 43-62). As shown in FIG. 3, significant sequence homology exists between the peptides encoded by the obtained DNA fragments (SEQ ID NOs: 44-62) and corresponding peptide sequences from EGIII (SEQ ID NO: 43). Due to this homology, it was concluded by Applicants that the nature of the numerous conserved residues identify the fragment as corresponding to a gene encoding a cellulase. Moreover, the high homology and strong conservation of residues corresponding to peptides (a), (b), (c) and/or (d), as in EGIII, identify the genes as coding an EGIII like enzyme from each of the organisms. FIG. 4 illustrates the percent similarity of the protein fragments sequenced.

From the sequenced fragments, it was possible to use the RAGE technique (rapid amplification of genomic ends) to rapidly obtain the sequence of the full length gene. Full length genes were obtained and are provided with several additional EGIII-like cellulase sequences in FIG. 6 (SEQ ID NOs: 8-29). As shown in FIG. 6, full length genes isolated from *Hypocrea schweinitzii* (SEQ ID NO: 9), *Aspergillus aculeatus* (SEQ ID NO: 10), *Aspergillus kawachii* (1) (SEQ ID NO: 11), *Aspergillus kawachii* (2) (SEQ ID NO: 12), *Aspergillus oryzae* (SEQ ID NO: 13), *Humicola grisea* (SEQ ID NO: 14), *Humicola insolens* (SEQ ID NO: 15), *Chaetomium brasilliense* (SEQ ID NO: 16), *Fusarium equiseti* (SEQ ID NO: 17), *Fusarium javanicum* (1) (SEQ ID NO: 18), *Fusarium javanicum* (2) (SEQ ID NO: 19), *Gliocladium roseum* (1) (SEQ ID NO: 20), *Gliocladium roseum* (2) (SEQ ID NO: 21), *Gliocladium roseum* (3) (SEQ ID NO: 22), *Gliogladium roseum* (4) (SEQ ID NO: 23), *Memnoniella echinata* (SEQ ID NO: 24), *Actinomycete* 11*AG*8 (SEQ ID NO: 26), *Streptomyces lividans CelB* (SEQ ID NO: 27), *Rhodothermus marinus* (SEQ ID NO: 28), *Emericella desertoru* (SEQ ID NO: 25), and *Erwinia carotovara* (SEQ ID NO: 29) all comprise significant homology EGIII from *Trichoderma reesei*.

The invention claimed is:

1. A method for obtaining a gene encoding an EGIII like cellulase comprising the steps of
   (i) preparing genomic DNA from an organism of interest;
   (ii) preparing a DNA primer encoding an amino acid string selected from the group consisting of one or more of the following:
      (a) Asn-Asn-(Xaa)-Trp-Gly (SEQ ID NO: 1), wherein (Xaa) at position 3 is Leu, Phe, Lys or Ile;
      (b) Glu-(Xaa)-Met-Ile-Trp (SEQ ID NO: 2), wherein (Xaa) at position 2 is Phe or Ile;
      (c) Gly-Thr-Glu-Pro-Phe-Thr (SEQ ID NO: 3);
      (d) (Xaa)-(Xaa)-(Xaa)-(Xaa)-(Xaa) (SEQ ID NO: 42), wherein (Xaa) at position 1 is Ser, Tyr, Cys, Trp, Thr, Asn, Lys, or Arg, (Xaa) at position 2 is Val or Pro, (Xaa) at position 3 is Lys or Ala, (Xaa) at position 4 is Ser or Ala, and (Xaa) at position 5 is Tyr or Phe; and
      (e) Lys-Asn-Phe-Phe-Asn-Tyr (SEQ ID NO: 5);
   (iii) mixing said genomic DNA from step (i) and said DNA primer from step (ii) under conditions suitable for the identification of all or part of a gene fragment in said genomic DNA corresponding to said DNA primer; and
   (iv) isolating said all or part of said gene corresponding to said fragment from said genomic DNA.

2. The method according to claim 1, wherein said step (iii) further comprises labeling said DNA primer and performing hybridization between said labeled DNA primer and said genomic DNA and detecting said hybridized genomic DNA which encodes all or part of an EGIII like cellulase.

3. The method according to claim 1, wherein, said step (iii) further comprises initiating a PCR reaction between said DNA primer and said genomic DNA and identifying a resulting amplified DNA fragment which comprises all or part of a gene encoding an EGIII like cellulase.

4. The method according to claim 1, wherein said genomic DNA is obtained from a bacteria, fungus or Actinomycete.

5. A method for obtaining a gene encoding an EGIII like cellulase comprising the steps of:
   (i) preparing genomic DNA from an organism of interest;
   (ii) preparing a DNA primer encoding an amino acid string selected from the group consisting of one or more of the following:
      (a) Asn-Asn-(Xaa)-Trp-Gly (SEQ ID NO: 1), wherein (Xaa) at position 3 is Leu, Phe, Lys or Ile;

(b) Glu-(Xaa)-Met-Ile-Trp (SEQ ID NO: 2), wherein (Xaa) at position 2 is Phe or Ile;

(c) Gly-Thr-Glu-Pro-Phe-Thr (SEQ ID NO: 3)

(d) (Xaa)-(Xaa)-(Xaa)-(Xaa)-(Xaa) (SEQ ID NO: 42), wherein (Xaa) at position 1 is Ser, Tyr, Cys, Trp, Thr, Asn, Lys, or Arg, (Xaa) at position 2 is Val or Pro, (Xaa) at position 3 is Lys or Ala, (Xaa) at position 4 is Ser or Ala, and (Xaa) at position 5 is Tyr or Phe; and (e) Lys-Asn-Phe-Phe-Asn-Tyr (SEQ ID NO: 5);

(iii) amplifying the genomic DNA from step (i) by the polymerase chain reaction (PCR) using DNA primers encoding amino acid strings (a), (d), (c) and (e); (a), (c) and (e); (d), (c) and (e); (a), (d) and (c); (a), (d) and (e); (a) and (c); (a) and (e); (d) and (c); or (d) and (e), under conditions suitable for producing one or more gene fragments from said genomic DNA;

(iv) selecting and pooling the gene fragments amplified in step (iii) and reamplifying using DNA primers encoding amino acid strings (a), (d) and (b); (a) and (b); or (d) and (b), or using DNA primers encoding amino acid strings (c), (e) and (b); (c) and (b); or (e) and (b) to produce one or more further gene fragments; and (v) isolating from said genomic DNA all or part of the gene corresponding to one or more the further gene fragments produced in step (iv).

6. The method according to claim 1, wherein said step (iii) further comprises labeling said DNA primer and performing hybridization between said labeled DNA primer and said genomic DNA and detecting said hybridized genomic DNA which encodes all or part of an EGIII like cellulase.

7. The method according to claim 5 or claim 6, wherein the gene fragments are selected by running the amplification products on a polyacrylamide gel and selecting gene fragments of a suitable size range.

8. The method according to claim 5, wherein gene fragments in the size range of 400-1000 base pairs are selected in step (iii).

9. The method according to claim 5, wherein gene fragments in the size range of 250-500 base pairs are selected in step (iv).

10. The method of claim 5, further comprising sequencing one or more of the gene fragments produced in step (iv).

11. The method according to claim 5, wherein said genomic DNA is obtained from a bacteria, fungus or Actinomycete.

12. The method according to claim 11, wherein said fungus is a filamentous fungus.

13. The method according to claim 12, wherein said filamentous fungus belongs to Euascomycete.

14. The method according to claim 13, wherein said Euascomycete belongs to Plectomycete.

15. The method according to claim 13, wherein said Euascomycete belongs to Diaporthales, Halosphaeriales, Microascales, Ophiostomatales, Phyllachorales, Sordariales or Xylariales.

16. The method according to claim 13, wherein said Euascomycete belongs to Hypocreales comprising Clavicipitaceae, Melanosporaceae, Nectriaceae, Niessliaceae or Mitosporic Hypocreales.

17. The method according to claim 13, wherein said Euascomycete belongs to Hypocreaceae, wherein said Hypocreaceae does not comprise Trichoderma.

18. The method according to claim 13, wherein said Euascomycete is *Gliocladium* spp., *Fusarium* spp., *Acremonium* spp., *Myceliophtora* spp., *Verticillium* ssp., *Myrothecium* ssp., or *Penicillium* ssp.

19. The method according to claim 13, wherein said Euascomycete is an *Aspergillus* comprising *A. aeneus, A. anthodesmis, A. aureofulgens, A. aureolatus, A. avenaceus, A. awamorii, A. bisporus, A. brunneouniseriatus, A. campestris, A. caesiellus, A. candidus, A. carbonarius, A. carneus, A. cervinus, A. clavatoflavus, A. clavatoanicus, A. clavatus, A. conicus, A. conjunctus, A. crustosus, A. deflectus, A. dimorphicus, A. eburneocremeus, A. egyptiacus, A. ellipticus, A. elongatus, A. ficuum, A. flaschentraegeri, A. flavus, a. fumigatus, A. giganteus, A. glaucus, A. gorakhpurensis, A. gracilis, A. iizuke, A. itaconicus, A. japonicus, A. kambarensis, A. kanagawaensis, A. lanosus, A. leporis, A. longivesica, A. mellinus, A. multicolor, A. niger, A. nomius, A. nutans, A. ochraceus, A. oryzae, A. pallidus, A. panamensis, A. parasiticus, A. parvulus, A. penicillioides, A. phialisepticus, A. phoenicis, A. proliferans, A. pulvinus, A. puniceus, A. raperi, A. recurvatus, A. restrictus, A. shirousami, A. sojae, A. sparsus, A. subolivaceus, A. subsessilis, A. tamarii, A. terreus, A. terricola, A. thomii, A. tubingensis, A. unguis, A. unilateralis, A. ustus, A. versicolor, A. wentii, A. xerophilus, A. zonatus*, A.sp.

20. A method for obtaining a gene encoding an EGIII like cellulase comprising the steps of:

(i) preparing genomic DNA from an organism of interest;

(ii) preparing degenerate primers encoding an amino acid string selected from the group consisting of one or more of the following:

(a) Asn-Asn-(Xaa)-Trp-Gly (SEQ ID NO: 1), wherein (Xaa) at position 3 is Leu, Phe, Lys or Ile;

(b) Glu-(Xaa)-Met-Ile-Trp (SEQ ID NO: 2), wherein (Xaa) at position 2 is Phe or Ile;

(c) Gly-Thr-Glu-Pro-Phe-Thr (SEQ ID NO: 3);

(d) (Xaa)-(Xaa)-(Xaa)-(Xaa)-(Xaa) (SEQ ID NO: 42), wherein (Xaa) at position 1 is Ser, Tyr, Cys, Trp, Thr, Asn, Lys or Arg, (Xaa) at position 2 is Val or Pro, (Xaa) at position 3 is Lys or Ala, (Xaa) at position 4 is Ser or Ala, and (Xaa) at position 5 is Tyr or Phe; and (e) Lys-Asn-Phe-Phe-Asn-Tyr (SEQ ID NO: 5);

(iii) mixing the genomic DNA from step (i) and the degenerate primers from step (ii) under conditions suitable for the identification of the gene or a fragment thereof within the genomic DNA; and (iv) isolating the gene or fragment thereof wherein the gene or fragment thereof encodes a polypeptide having at least 60% amino acid identity to EGIII cellulase.

* * * * *

SEQUENCE LISTING

```
<160> NUMBER OF SEQ ID NOS: 68

<210> SEQ ID NO 1
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 3
<223> OTHER INFORMATION: Xaa = Leu, Phe, Lys, or Ile

<400> SEQUENCE: 1

Asn Asn Xaa Trp Gly
 1               5

<210> SEQ ID NO 2
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 2
<223> OTHER INFORMATION: Xaa = Leu, Phe, or Ile

<400> SEQUENCE: 2

Glu Xaa Met Ile Trp
 1               5

<210> SEQ ID NO 3
<211> LENGTH: 6
<212> TYPE: PRT
<213> ORGANISM: Artificial Sequence
<220> FEATURE:
<223> OTHER INFORMATION: synthetic

<400> SEQUENCE: 3

Gly Thr Glu Pro Phe Thr
 1               5
```

<210> SEQ ID NO 4
<211> LENGTH: 5
<212> TYPE: PRT
<213> ORGANISM: Artificial Sequence
<220> FEATURE:
<223> OTHER INFORMATION: synthetic

<400> SEQUENCE: 4

Ser Val Lys Ser Tyr
 1               5

<210> SEQ ID NO 5
<211> LENGTH: 6
<212> TYPE: PRT
<213> ORGANISM: Artificial Sequence
<220> FEATURE:
<223> OTHER INFORMATION: synthetic

<400> SEQUENCE: 5

Lys Asn Phe Phe Asn Tyr
 1               5

<210> SEQ ID NO 6
<211> LENGTH: 702
<212> TYPE: DNA
<213> ORGANISM: Trichoderma reesei

<400> SEQUENCE: 6

```
atgaagttcc ttcaagtcct ccctgccctc ataccggccg ccctggccca aaccagctgt     60
gaccagtggg caaccttcac tggcaacggc tacacagtca gcaacaacct tggggagca    120
tcagccggct ctggatttgg ctgcgtgacg gcggtatcgc tcagcggcgg ggcctcctgg    180
cacgcagact ggcagtggtc cggcggccag aacaacgtca agtcgtacca gaactctcag    240
attgccattc cccagaagag gaccgtcaac agcatcagca gcatgccac cactgccagc    300
tggagctaca gcgggagcaa catccgcgct aatgttgcgt atgacttgtt caccgcagcc    360
aacccgaatc atgtcacgta ctcgggagac tacgaactca tgatctggct tggcaaatac    420
ggcgatattg ggccgattgg gtcctcacag gaacagtca acgtcggtgg ccagagctgg    480
acgctctact atggctacaa cggagccatg caagtctatt cctttgtggc ccagaccaac    540
actaccaact acagcggaga tgtcaagaac ttcttcaatt atctccgaga caataaagga    600
tacaacgctg caggccaata tgttcttagc taccaatttg gtaccgagcc cttcacgggc    660
agtggaactc tgaacgtcgc atcctggacc gcatctatca ac                     702
```

<210> SEQ ID NO 7
<211> LENGTH: 232
<212> TYPE: PRT
<213> ORGANISM: Trichoderma reesei

<400> SEQUENCE: 7

Met Lys Phe Leu Gln Val Leu Pro Ala Leu Ile Pro Ala Ala Leu Ala
 1               5                  10                  15

Gln Thr Ser Cys Asp Gln Trp Ala Thr Phe Thr Gly Asn Gly Tyr Thr
             20                  25                  30

Val Ser Asn Asn Leu Trp Gly Ala Ser Ala Gly Ser Gly Phe Gly Cys
         35                  40                  45

Val Thr Ala Val Ser Leu Ser Gly Gly Ala His Ala Asp Trp Gln Trp
     50                  55                  60

Ser Gly Gly Gln Asn Asn Val Lys Ser Tyr Gln Asn Ser Gln Ile Ala
65                  70                  75                  80

```
Ile Pro Gln Lys Arg Thr Val Asn Ser Ile Ser Ser Met Pro Thr Thr
                85                  90                  95

Ala Ser Trp Ser Tyr Ser Gly Ser Asn Ile Arg Ala Asn Val Ala Tyr
            100                 105                 110

Asp Leu Phe Thr Ala Ala Asn Pro Asn His Val Thr Tyr Ser Gly Asp
        115                 120                 125

Tyr Glu Leu Met Ile Trp Leu Gly Lys Tyr Gly Asp Ile Gly Pro Ile
    130                 135                 140

Gly Ser Ser Gln Gly Thr Val Asn Val Gly Gly Gln Ser Trp Thr Leu
145                 150                 155                 160

Tyr Tyr Gly Tyr Asn Gly Ala Met Gln Val Tyr Ser Phe Val Ala Gln
                165                 170                 175

Thr Asn Thr Thr Asn Tyr Ser Gly Asp Val Lys Asn Phe Phe Asn Tyr
            180                 185                 190

Leu Arg Asp Asn Lys Gly Tyr Asn Ala Ala Gly Gln Tyr Val Leu Ser
        195                 200                 205

Tyr Gln Phe Gly Thr Glu Pro Phe Thr Gly Ser Gly Thr Leu Asn Val
    210                 215                 220

Ala Ser Trp Thr Ala Ser Ile Asn
225                 230

<210> SEQ ID NO 8
<211> LENGTH: 234
<212> TYPE: PRT
<213> ORGANISM: Trichoderma reesei

<400> SEQUENCE: 8

Met Lys Phe Leu Gln Val Leu Pro Ala Leu Ile Pro Ala Ala Leu Ala
  1               5                  10                  15

Gln Thr Ser Cys Asp Gln Trp Ala Thr Phe Thr Gly Asn Gly Tyr Thr
                20                  25                  30

Val Ser Asn Asn Leu Trp Gly Ala Ser Ala Gly Ser Gly Phe Gly Cys
            35                  40                  45

Val Thr Ala Val Ser Leu Ser Gly Gly Ala Ser Trp His Ala Asp Trp
        50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220
```

Asn Val Ala Ser Trp Thr Ala Ser Ile Asn
225                 230

<210> SEQ ID NO 9
<211> LENGTH: 234
<212> TYPE: PRT
<213> ORGANISM: Hypocrea schweinitzii

<400> SEQUENCE: 9

Met Lys Phe Leu Gln Val Leu Pro Ala Ile Leu Pro Ala Ala Leu Ala
1               5                   10                  15

Gln Thr Ser Cys Asp Gln Tyr Ala Thr Phe Ser Gly Asn Gly Tyr Ile
            20                  25                  30

Val Ser Asn Asn Leu Trp Gly Ala Ser Ala Gly Ser Gly Phe Gly Cys
        35                  40                  45

Val Thr Ser Val Ser Leu Asn Gly Ala Ala Ser Trp His Ala Asp Trp
    50                  55                  60

Gln Trp Ser Gly Gly Gln Asn Asn Val Lys Ser Tyr Gln Asn Val Gln
65                  70                  75                  80

Ile Asn Ile Pro Gln Lys Arg Thr Val Asn Ser Ile Gly Ser Met Pro
                85                  90                  95

Thr Thr Ala Ser Trp Ser Tyr Ser Gly Ser Asp Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Thr Trp
145                 150                 155                 160

Thr Leu Tyr Tyr Gly Tyr Asn Gly Ala Met Gln Val Tyr Ser Phe Val
                165                 170                 175

Ala Gln Ser Asn Thr Thr Ser Tyr Ser Gly Asp Val Lys Asn Phe Phe
            180                 185                 190

Asn Tyr Leu Arg Asp Asn Lys Gly Tyr Asn Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230

<210> SEQ ID NO 10
<211> LENGTH: 259
<212> TYPE: PRT
<213> ORGANISM: Aspergillus aculeatus

<400> SEQUENCE: 10

Met Lys Ala Phe His Leu Leu Ala Leu Ala Gly Ala Ala Val Ala
1               5                   10                  15

Gln Gln Ala Gln Leu Cys Asp Gln Tyr Ala Thr Tyr Thr Gly Gly Val
            20                  25                  30

Tyr Thr Ile Asn Asn Asn Leu Trp Gly Lys Asp Ala Gly Ser Gly Ser
        35                  40                  45

Gln Cys Thr Thr Val Asn Ser Ala Ser Ala Gly Thr Ser Trp Ser
    50                  55                  60

Thr Lys Trp Asn Trp Ser Gly Gly Glu Asn Ser Val Lys Ser Tyr Ala
65                  70                  75                  80

```
Asn Ser Gly Leu Thr Phe Asn Lys Lys Leu Val Ser Gln Ile Ser Gln
                85                  90                  95

Ile Pro Thr Thr Ala Arg Trp Ser Tyr Asp Asn Thr Gly Ile Arg Ala
            100                 105                 110

Asp Val Ala Tyr Asp Leu Phe Thr Ala Ala Asp Ile Asn His Val Thr
        115                 120                 125

Trp Ser Gly Asp Tyr Glu Leu Met Ile Trp Leu Ala Arg Tyr Gly Gly
    130                 135                 140

Val Gln Pro Ile Gly Ser Gln Ile Ala Thr Ala Thr Val Asp Gly Gln
145                 150                 155                 160

Thr Trp Glu Leu Trp Tyr Gly Ala Asn Gly Ser Gln Lys Thr Tyr Ser
                165                 170                 175

Phe Val Ala Pro Thr Pro Ile Thr Ser Phe Gln Gly Asp Val Asn Asp
            180                 185                 190

Phe Phe Lys Tyr Leu Thr Gln Asn His Gly Phe Pro Ala Ser Ser Gln
        195                 200                 205

Tyr Leu Ile Thr Leu Gln Phe Gly Thr Glu Pro Phe Thr Gly Gly Pro
    210                 215                 220

Ala Thr Leu Ser Val Ser Asn Trp Ser Ala Ser Val Gln Gln Ala Gly
225                 230                 235                 240

Phe Glu Pro Trp Gln Asn Gly Ala Gly Leu Ala Val Asn Ser Phe Ser
                245                 250                 255

Ser Thr Val

<210> SEQ ID NO 11
<211> LENGTH: 239
<212> TYPE: PRT
<213> ORGANISM: Aspergillus kawachii (1)

<400> SEQUENCE: 11

Met Lys Leu Ser Met Thr Leu Ser Leu Phe Ala Ala Thr Ala Met Gly
  1               5                  10                  15

Gln Thr Met Cys Ser Gln Tyr Asp Ser Ala Ser Ser Pro Pro Tyr Ser
                20                  25                  30

Val Asn Gln Asn Leu Trp Gly Glu Tyr Gln Gly Thr Gly Ser Gln Cys
            35                  40                  45

Val Tyr Val Asp Lys Leu Ser Ser Ser Gly Ala Ser Trp His Thr Lys
        50                  55                  60

Trp Thr Trp Ser Gly Gly Glu Gly Thr Val Lys Ser Tyr Ser Asn Ser
65                  70                  75                  80

Gly Leu Thr Phe Asp Lys Lys Leu Val Ser Asp Val Ser Ser Ile Pro
                85                  90                  95

Thr Ser Val Thr Trp Ser Gln Asp Asp Thr Asn Val Gln Ala Asp Val
            100                 105                 110

Ser Tyr Asp Leu Phe Thr Ala Ala Asn Ala Asp His Ala Thr Ser Ser
        115                 120                 125

Gly Asp Tyr Glu Leu Met Ile Trp Leu Ala Arg Tyr Gly Ser Val Gln
    130                 135                 140

Pro Ile Gly Lys Gln Ile Ala Thr Ala Thr Val Gly Gly Lys Ser Trp
145                 150                 155                 160

Glu Val Trp Tyr Gly Thr Ser Thr Gln Ala Gly Ala Glu Gln Lys Thr
                165                 170                 175

Tyr Ser Phe Val Ala Gly Ser Pro Ile Asn Ser Trp Ser Gly Asp Ile
            180                 185                 190

Lys Asp Phe Phe Asn Tyr Leu Thr Gln Asn Gln Gly Phe Pro Ala Ser
```

```
                195                 200                 205
Ser Gln His Leu Ile Thr Leu Gln Cys Gly Thr Glu Pro Phe Thr Gly
            210                 215                 220

Gly Pro Ala Thr Phe Thr Val Asp Asn Trp Thr Ala Ser Val Asn
225                 230                 235

<210> SEQ ID NO 12
<211> LENGTH: 239
<212> TYPE: PRT
<213> ORGANISM: Aspergillus kawachii (2)

<400> SEQUENCE: 12

Met Lys Ala Phe His Leu Leu Ala Ala Leu Ser Gly Ala Val Ala
1               5                   10                  15

Gln Gln Ala Gln Leu Cys Asp Gln Tyr Ala Thr Tyr Thr Gly Gly Val
            20                  25                  30

Tyr Thr Ile Asn Asn Asn Leu Trp Gly Lys Asp Ala Gly Ser Gly Ser
                35                  40                  45

Gln Cys Thr Thr Val Asn Ser Ala Ser Ser Ala Gly Thr Ser Trp Ser
    50                  55                  60

Thr Lys Trp Asn Trp Ser Gly Gly Glu Asn Ser Val Lys Ser Tyr Ala
65              70                  75                  80

Asn Ser Gly Leu Ser Phe Asn Lys Lys Leu Val Ser Gln Ile Ser His
                85                  90                  95

Ile Pro Thr Ala Ala Arg Trp Ser Tyr Asp Asn Thr Cys Ile Arg Arg
            100                 105                 110

Gly Arg Ala Tyr Asp Leu Phe Thr Ala Ala Asp Ile Asn His Val Thr
        115                 120                 125

Trp Ser Gly Asp Tyr Glu Leu Met Ile Trp Leu Ala Arg Tyr Gly Gly
    130                 135                 140

Val Gln Pro Leu Gly Ser Gln Ile Ala Thr Ala Thr Val Glu Gly Gln
145                 150                 155                 160

Thr Trp Glu Leu Trp Tyr Gly Val Asn Gly Ala Gln Lys Thr Tyr Ser
                165                 170                 175

Phe Val Ala Ala Asn Pro Ile Thr Ser Phe Gln Gly Asp Ile Asn Asp
            180                 185                 190

Phe Phe Lys Tyr Leu Thr Gln Asn His Gly Phe Pro Ala Ser Ser Gln
        195                 200                 205

Tyr Leu Ile Ile Leu Ala Leu Gln Phe Gly Thr Glu Pro Phe Thr Gly
    210                 215                 220

Gly Pro Ala Thr Leu Asn Val Ala Asp Trp Ser Ala Ser Val Gln
225                 230                 235

<210> SEQ ID NO 13
<211> LENGTH: 247
<212> TYPE: PRT
<213> ORGANISM: Aspergillus oryzae

<400> SEQUENCE: 13

Met Lys Leu Ser Leu Ala Leu Ala Thr Leu Val Ala Thr Ala Phe Ser
1               5                   10                  15

Gln Glu Leu Cys Ala Gln Tyr Asp Ser Ala Ser Ser Pro Pro Tyr Ser
            20                  25                  30

Val Asn Asn Asn Leu Trp Gly Gln Asp Ser Gly Thr Gly Phe Thr Ser
                35                  40                  45

Gln Cys Val Tyr Val Asp Asn Leu Ser Ser Ser Gly Ala Ala Trp His
    50                  55                  60
```

```
Thr Thr Trp Thr Trp Asn Gly Glu Gly Ser Val Lys Ser Tyr Ser
 65                  70                  75                  80

Asn Ser Ala Val Thr Phe Asp Lys Lys Leu Val Ser Asp Val Gln Ser
             85                  90                  95

Ile Pro Thr Asp Val Glu Trp Ser Gln Asp Phe Thr Asn Thr Asn Val
            100                 105                 110

Asn Ala Asp Val Ala Tyr Asp Leu Phe Thr Ala Ala Asp Gln Asn His
        115                 120                 125

Val Thr Tyr Ser Gly Asp Tyr Glu Leu Met Ile Trp Leu Ala Arg Tyr
    130                 135                 140

Gly Thr Ile Gln Pro Ile Gly Thr Gln Ile Asp Thr Ala Thr Val Glu
145                 150                 155                 160

Gly His Thr Trp Glu Leu Trp Phe Thr Tyr Gly Thr Thr Ile Gln Ala
                165                 170                 175

Gly Ala Glu Gln Lys Thr Tyr Ser Phe Val Ser Ala Thr Pro Ile Asn
            180                 185                 190

Thr Phe Gly Gly Asp Ile Lys Lys Phe Phe Asp Tyr Ile Thr Ser Lys
        195                 200                 205

His Ser Phe Pro Ala Ser Ala Gln Tyr Leu Ile Asn Met Gln Phe Gly
    210                 215                 220

Thr Glu Pro Phe Phe Thr Thr Gly Gly Pro Val Thr Phe Thr Val Pro
225                 230                 235                 240

Asn Trp Thr Ala Ser Val Asn
                245

<210> SEQ ID NO 14
<211> LENGTH: 254
<212> TYPE: PRT
<213> ORGANISM: Humicola grisei

<400> SEQUENCE: 14

Met Leu Lys Ser Ala Leu Leu Leu Gly Ala Ala Ala Val Ser Val Gln
  1               5                  10                  15

Ser Ala Ser Ile Pro Thr Ile Pro Ala Asn Leu Glu Pro Arg Gln Ile
             20                  25                  30

Arg Ser Leu Cys Glu Leu Tyr Gly Tyr Trp Ser Gly Asn Gly Tyr Glu
         35                  40                  45

Leu Leu Asn Asn Leu Trp Gly Lys Asp Thr Ala Thr Ser Gly Trp Gln
 50                  55                  60

Cys Thr Tyr Leu Asp Gly Thr Asn Asn Gly Gly Ile Gln Trp Asn Thr
 65                  70                  75                  80

Ala Trp Glu Trp Gln Gly Ala Pro Asp Asn Val Lys Asn Tyr Pro Tyr
             85                  90                  95

Val Gly Lys Gln Ile Gln Arg Gly Arg Lys Ile Ser Asp Ile Asn Ser
            100                 105                 110

Met Arg Thr Ser Val Ser Trp Thr Tyr Asp Arg Thr Asp Leu Arg Ala
        115                 120                 125

Asn Val Ala Tyr Asp Val Phe Thr Ala Arg Asp Pro Asp His Pro Asn
    130                 135                 140

Trp Gly Gly Asp Tyr Glu Leu Met Ile Trp Leu Ala Arg Tyr Gly Gly
145                 150                 155                 160

Ile Tyr Pro Ile Gly Thr Phe His Ser Gln Val Asn Leu Ala Gly Arg
                165                 170                 175

Thr Trp Asp Leu Trp Thr Gly Tyr Asn Gly Asn Met Arg Val Tyr Ser
            180                 185                 190
```

```
Phe Leu Pro Pro Ser Gly Asp Ile Arg Asp Phe Ser Cys Asp Ile Lys
            195                 200                 205

Asp Phe Phe Asn Tyr Leu Glu Arg Asn His Gly Tyr Pro Ala Arg Glu
        210                 215                 220

Gln Asn Leu Ile Val Tyr Gln Val Gly Thr Glu Cys Phe Thr Gly Gly
225                 230                 235                 240

Pro Ala Arg Phe Thr Cys Arg Asp Phe Arg Ala Asp Leu Trp
                245                 250

<210> SEQ ID NO 15
<211> LENGTH: 254
<212> TYPE: PRT
<213> ORGANISM: Humicola insolens

<400> SEQUENCE: 15

Met Leu Lys Ser Ala Leu Leu Gly Pro Ala Ala Val Ser Val Gln
1               5                   10                  15

Ser Ala Ser Ile Pro Thr Ile Pro Ala Asn Leu Glu Pro Arg Gln Ile
            20                  25                  30

Arg Ser Leu Cys Glu Leu Tyr Gly Tyr Trp Ser Gly Asn Gly Tyr Glu
        35                  40                  45

Leu Leu Asn Asn Leu Trp Gly Lys Asp Thr Ala Thr Ser Gly Trp Gln
50                  55                  60

Cys Thr Tyr Leu Asp Gly Thr Asn Asn Gly Gly Ile Gln Trp Ser Thr
65                  70                  75                  80

Ala Trp Glu Trp Gln Gly Ala Pro Asp Asn Val Lys Ser Tyr Pro Tyr
                85                  90                  95

Val Gly Lys Gln Ile Gln Arg Gly Arg Lys Ile Ser Asp Ile Asn Ser
            100                 105                 110

Met Arg Thr Ser Val Ser Trp Thr Tyr Asp Arg Thr Asp Ile Arg Ala
        115                 120                 125

Asn Val Ala Tyr Asp Val Phe Thr Ala Arg Asp Pro Asp His Pro Asn
130                 135                 140

Trp Gly Gly Asp Tyr Glu Leu Met Ile Trp Leu Ala Arg Tyr Gly Gly
145                 150                 155                 160

Ile Tyr Pro Ile Gly Thr Phe His Ser Gln Val Asn Leu Ala Gly Arg
                165                 170                 175

Thr Trp Asp Leu Trp Thr Gly Tyr Asn Gly Asn Met Arg Val Tyr Ser
            180                 185                 190

Phe Leu Pro Pro Ser Gly Asp Ile Arg Asp Phe Ser Cys Asp Ile Lys
        195                 200                 205

Asp Phe Phe Asn Tyr Leu Glu Arg Asn His Gly Tyr Pro Ala Arg Glu
210                 215                 220

Gln Asn Leu Ile Val Tyr Gln Val Gly Thr Glu Cys Phe Thr Gly Gly
225                 230                 235                 240

Pro Ala Arg Phe Thr Cys Arg Asp Phe Arg Ala Asp Leu Trp
                245                 250

<210> SEQ ID NO 16
<211> LENGTH: 247
<212> TYPE: PRT
<213> ORGANISM: Chaetomium brasiliense

<400> SEQUENCE: 16

Met Lys Leu Thr Leu Val Leu Phe Val Ser Ser Leu Ala Ala Ala Thr
1               5                   10                  15
```

```
Pro Leu Gly Trp Arg Glu Arg Gln Gln Val Ser Leu Cys Gly Gln
            20                  25                  30

Ser Ser Ser Trp Ser Gly Asn Gly Tyr Gln Leu Asn Asn Leu Trp
        35                  40                  45

Gly Gln Ser Arg Ala Thr Ser Gly Ser Gln Cys Thr Tyr Leu Asp Ser
 50                  55                  60

Ser Ser Asn Ser Gly Ile His Trp His Thr Thr Trp Thr Trp Glu Gly
 65                  70                  75                  80

Gly Glu Gly Glu Val Lys Ser Tyr Ala Tyr Ser Gly Arg Gln Val Ser
                85                  90                  95

Thr Gly Leu Thr Ile Ala Ser Ile Asp Ser Met Gln Thr Ser Val Ser
            100                 105                 110

Trp Glu Tyr Asn Thr Thr Asp Ile Gln Ala Asn Val Ala Tyr Asp Ile
        115                 120                 125

Phe Thr Ala Glu Asp Pro Asp His Glu His Ser Ser Gly Asp Tyr Glu
    130                 135                 140

Leu Met Ile Trp Leu Ala Arg Tyr Asn Asn Val Ser Pro Ile Gly Ser
145                 150                 155                 160

Ser Val Ala Thr Ala Thr Val Gly Gly Asp Thr Trp Asp Leu Phe Ala
                165                 170                 175

Gly Ala Asn Gly Asp Met Glu Val Tyr Ser Phe Val Ala Glu Asn Thr
            180                 185                 190

Met Asn Ser Phe Ser Gly Asp Val Lys Asp Phe Phe Asp Tyr Leu Glu
        195                 200                 205

Gln Asn Val Gly Phe Pro Val Asp Asp Gln Tyr Leu Leu Val Phe Glu
    210                 215                 220

Leu Gly Ser Glu Ala Phe Thr Gly Gly Pro Ala Thr Leu Ser Val Ser
225                 230                 235                 240

Gln Phe Ser Ala Asn Ile Ala
                245

<210> SEQ ID NO 17
<211> LENGTH: 238
<212> TYPE: PRT
<213> ORGANISM: Fusarium equseti

<400> SEQUENCE: 17

Met Lys Ser Thr Leu Leu Ala Gly Ala Phe Ala Pro Leu Ala Phe
 1               5                  10                  15

Ala Lys Asp Leu Cys Glu Gln Tyr Gly Tyr Leu Ser Ser Asp Gly Tyr
            20                  25                  30

Ser Leu Asn Asn Asn Val Trp Gly Lys Asp Ser Gly Thr Gly Asp Gln
        35                  40                  45

Cys Thr His Val Asn Trp Asn Asn Ala Asn Gly Ala Gly Trp Asp Val
 50                  55                  60

Glu Trp Asn Trp Ser Gly Gly Lys Asp Asn Val Lys Ser Tyr Pro Asn
 65                  70                  75                  80

Ser Ala Leu Leu Ile Gly Glu Asp Lys Lys Thr Ile Ser Ser Ile Thr
                85                  90                  95

Asn Met Gln Ser Thr Ala Glu Trp Lys Tyr Ser Gly Asp Asn Leu Arg
            100                 105                 110

Ala Asp Val Ala Tyr Asp Leu Phe Thr Ala Ala Asp Pro Asn His Glu
        115                 120                 125

Thr Ser Ser Gly Glu Tyr Glu Leu Met Val Trp Leu Ala Arg Ile Gly
    130                 135                 140
```

```
Gly Val Gln Pro Ile Gly Ser Leu Gln Thr Ser Val Thr Ile Glu Gly
145                 150                 155                 160

His Thr Trp Glu Leu Trp Val Gly Met Asn Gly Ser Met Lys Val Phe
                165                 170                 175

Ser Phe Val Ala Pro Thr Pro Val Asn Asn Phe Asn Ala Asp Ile Lys
            180                 185                 190

Gln Phe Trp Asp Tyr Leu Thr Lys Ser Gln Asn Phe Pro Ala Asp Asn
        195                 200                 205

Gln Tyr Leu Leu Thr Phe Gln Phe Gly Thr Glu Pro Phe Thr Gly Asp
    210                 215                 220

Asn Ala Lys Phe Thr Val Thr Asn Phe Asn Ala His Leu Lys
225                 230                 235
```

<210> SEQ ID NO 18
<211> LENGTH: 244
<212> TYPE: PRT
<213> ORGANISM: Fusarium javanicum (1)

<400> SEQUENCE: 18

```
Met Lys Ser Ala Ile Val Ala Ala Leu Ala Gly Leu Ala Ala Ala Ser
1               5                   10                  15

Pro Thr Arg Leu Ile Pro Arg Gly Gln Phe Cys Gly Gln Trp Asp Ser
            20                  25                  30

Glu Thr Ala Gly Ala Tyr Thr Ile Tyr Asn Asn Leu Trp Gly Lys Asp
        35                  40                  45

Asn Ala Glu Ser Gly Glu Gln Cys Thr Thr Asn Ser Gly Glu Gln Ser
    50                  55                  60

Asp Gly Ser Ile Ala Trp Ser Val Glu Trp Ser Trp Thr Gly Gly Gln
65                  70                  75                  80

Gly Gln Val Lys Ser Tyr Pro Asn Ala Val Val Glu Ile Glu Lys Lys
                85                  90                  95

Thr Leu Gly Glu Val Ser Ser Ile Pro Ser Ala Trp Asp Trp Thr Tyr
            100                 105                 110

Thr Gly Asn Gly Ile Ile Ala Asn Val Ala Tyr Asp Leu Phe Thr Ser
        115                 120                 125

Ser Thr Glu Ser Gly Asp Ala Glu Tyr Glu Phe Met Ile Trp Leu Ser
    130                 135                 140

Ala Leu Gly Gly Ala Gly Pro Ile Ser Asn Asp Gly Ser Pro Val Ala
145                 150                 155                 160

Thr Ala Glu Leu Ala Gly Thr Ser Trp Lys Leu Tyr Gln Gly Lys Asn
                165                 170                 175

Asn Gln Met Thr Val Phe Ser Phe Val Ala Glu Ser Asp Val Asn Asn
            180                 185                 190

Phe Cys Gly Asp Leu Ala Asp Phe Thr Asp Tyr Leu Val Asp Asn His
        195                 200                 205

Gly Val Ser Ser Ser Gln Ile Leu Gln Ser Val Gly Ala Gly Thr Glu
    210                 215                 220

Pro Phe Glu Gly Thr Asn Ala Val Phe Thr Thr Asn Asn Tyr His Ala
225                 230                 235                 240

Asp Val Glu Tyr
```

<210> SEQ ID NO 19
<211> LENGTH: 250
<212> TYPE: PRT
<213> ORGANISM: Fusarium javanicum (2)

<400> SEQUENCE: 19

```
Met Lys Phe Phe Gly Val Val Ser Ala Ser Leu Ala Ala Thr Ala Val
 1               5                  10                  15

Ala Thr Pro Thr Thr Pro Thr Glu Thr Ile Glu Lys Arg Asp Thr Thr
                20                  25                  30

Trp Cys Asp Ala Phe Gly Ser Leu Ala Thr Ser Gly Tyr Thr Val Tyr
            35                  40                  45

His Asn Asn Trp Gly Lys Gly Asp Ala Thr Ser Gly Gln Cys Thr
 50                  55                  60

Thr Phe Thr Ser Val Ser Asn Asn Phe Val Trp Ser Thr Ser Trp
 65                  70                  75                  80

Thr Trp Ala Gly Gly Ala Gly Lys Val Lys Ser Tyr Ser Asn Val Ala
                85                  90                  95

Leu Glu Lys Ile Asn Lys Lys Ile Ser Asp Ile Lys Ser Val Ser Thr
                100                 105                 110

Arg Trp Ile Trp Arg Tyr Thr Gly Thr Lys Met Ile Ala Asn Val Ser
            115                 120                 125

Tyr Asp Leu Trp Phe Ala Pro Thr Ala Ser Ser Asn Asn Ala Tyr Glu
 130                 135                 140

Ile Met Ile Trp Val Gly Ala Tyr Gly Gly Ala Leu Pro Ile Ser Thr
145                 150                 155                 160

Pro Gly Lys Gly Val Ile Asp Arg Pro Thr Leu Ala Gly Ile Pro Trp
                165                 170                 175

Asp Val Tyr Lys Gly Pro Asn Gly Asp Val Thr Val Ile Ser Phe Val
            180                 185                 190

Ala Ser Ser Asn Gln Gly Asn Phe Gln Ala Asp Leu Lys Glu Phe Leu
            195                 200                 205

Asn Tyr Leu Thr Ser Lys Gln Gly Leu Pro Ser Asn Tyr Val Ala Thr
            210                 215                 220

Ser Phe Gln Ala Gly Thr Glu Pro Phe Glu Gly Thr Asn Ala Val Leu
225                 230                 235                 240

Lys Thr Ser Ala Tyr Thr Ile Ser Val Asn
                245                 250

<210> SEQ ID NO 20
<211> LENGTH: 238
<212> TYPE: PRT
<213> ORGANISM: Gliocladium roseum (1)

<400> SEQUENCE: 20

Met Lys Ala Asn Ile Val Ile Leu Ser Leu Phe Ala Pro Leu Ala Ala
 1               5                  10                  15

Val Ala Gln Thr Leu Cys Gly Gln Tyr Ser Ser Asn Thr Gln Gly Gly
                20                  25                  30

Tyr Ile Phe Asn Asn Asn Met Trp Gly Met Gly Ser Gly Ser Gly Ser
            35                  40                  45

Gln Cys Thr Tyr Val Asp Lys Val Trp Ala Glu Gly Val Ala Trp His
 50                  55                  60

Thr Asp Trp Ser Trp Ser Gly Gly Asp Asn Val Lys Ser Tyr Pro
 65                  70                  75                  80

Tyr Ser Gly Arg Glu Leu Gly Thr Lys Arg Ile Val Ser Ser Ile Lys
                85                  90                  95

Ser Ile Ser Ser Gly Ala Asp Trp Asp Tyr Thr Gly Ser Asn Leu Arg
            100                 105                 110

Ala Asn Ala Ala Tyr Asp Ile Phe Thr Ser Ala Asn Pro Asn His Ala
            115                 120                 125
```

Thr Ser Ser Gly Asp Tyr Glu Val Met Ile Trp Leu Ala Asn Leu Gly
    130                 135                 140

Gly Leu Thr Pro Ile Gly Ser Pro Ile Gly Thr Val Lys Ala Ala Gly
145                 150                 155                 160

Arg Asp Trp Glu Leu Trp Asp Gly Tyr Asn Gly Ala Met Arg Val Tyr
                165                 170                 175

Ser Phe Val Ala Pro Ser Gln Leu Asn Ser Phe Asp Gly Glu Ile Met
            180                 185                 190

Asp Phe Phe Tyr Val Val Lys Asp Met Arg Gly Phe Pro Ala Asp Ser
        195                 200                 205

Gln His Leu Leu Thr Val Gln Phe Gly Thr Glu Pro Ile Ser Gly Ser
    210                 215                 220

Gly Ala Lys Phe Ser Val Ser His Trp Ser Ala Lys Leu Gly
225                 230                 235

<210> SEQ ID NO 21
<211> LENGTH: 348
<212> TYPE: PRT
<213> ORGANISM: Gliocladium roseum (2)

<400> SEQUENCE: 21

Met Lys Ser Ile Ile Ser Phe Phe Gly Leu Ala Thr Leu Val Ala Ala
1               5                   10                  15

Ala Pro Ser Gln Asn Pro Thr Arg Thr Gln Pro Leu Glu Lys Arg Ala
            20                  25                  30

Thr Thr Leu Cys Gly Gln Trp Asp Ser Val Thr Gly Gly Tyr Thr
        35                  40                  45

Ile Tyr Asn Asn Leu Trp Gly Gln Asp Asn Gly Ser Gly Ser Gln Cys
    50                  55                  60

Leu Thr Val Glu Gly Val Thr Asp Gly Leu Ala Ala Trp Ser Ser Thr
65                  70                  75                  80

Trp Ser Trp Ser Gly Gly Ser Ser Val Lys Ser Tyr Ser Asn Ala
                85                  90                  95

Val Leu Ser Ala Glu Ala Ala Arg Ile Ser Ala Ile Ser Ser Ile Pro
            100                 105                 110

Ser Lys Trp Glu Trp Ser Tyr Thr Gly Thr Asp Ile Val Ala Asn Val
        115                 120                 125

Ala Tyr Asp Leu Phe Ser Asn Thr Asp Cys Gly Asp Thr Pro Glu Tyr
    130                 135                 140

Glu Ile Met Ile Trp Leu Ser Ala Leu Gly Ala Gly Pro Ile Ser
145                 150                 155                 160

Ser Thr Gly Ser Ser Ile Ala Thr Val Thr Ile Ala Gly Ala Ser Trp
                165                 170                 175

Asn Leu Trp Gln Gly Gln Asn Asn Gln Met Ala Val Phe Ser Phe Val
            180                 185                 190

Ala Glu Ser Asp Gln Lys Ser Phe Ser Gly Asp Leu Asn Asp Phe Ile
        195                 200                 205

Gln Tyr Leu Val Asp Ser Gln Gly Tyr Ser Gly Ser Gln Cys Leu Tyr
    210                 215                 220

Ser Ile Gly Ala Gly Thr Glu Pro Phe Thr Gly Thr Asp Ala Glu Phe
225                 230                 235                 240

Ile Thr Thr Gly Tyr Ser Val Ser Val Ser Ala Gly Asp Ser Gly Cys
                245                 250                 255

Asp Glu Thr Thr Thr Ser Ser Gln Ala Gln Ser Ser Thr Val Glu Thr
            260                 265                 270

```
Ser Thr Ala Thr Gln Pro Gln Ser Ser Thr Val Val Pro Thr Val
        275                 280                 285

Thr Leu Ser Gln Pro Ser Asn Glu Ser Thr Thr Thr Pro Val Gln Ser
        290                 295                 300

Gln Pro Ser Ser Val Glu Thr Thr Pro Thr Ala Gln Pro Gln Ser Ser
305                 310                 315                 320

Ser Val Gln Thr Thr Thr Thr Ala Gln Ala Gln Pro Thr Ser Gly Thr
                325                 330                 335

Gly Cys Ser Arg Arg Arg Lys Arg Arg Ala Val Val
            340                 345
```

<210> SEQ ID NO 22
<211> LENGTH: 236
<212> TYPE: PRT
<213> ORGANISM: Gliocladium roseum (3)

<400> SEQUENCE: 22

```
Met Lys Phe Gln Leu Leu Ser Leu Thr Ala Phe Ala Pro Leu Ser Leu
1               5                   10                  15

Ala Ala Leu Cys Gly Gln Tyr Gln Ser Gln Ser Gln Gly Gly Tyr Ile
            20                  25                  30

Phe Asn Asn Lys Trp Gly Gln Gly Ser Gly Ser Gly Ser Gln Cys
        35                  40                  45

Leu Thr Ile Asp Lys Thr Trp Asp Ser Asn Val Ala Phe His Ala Asp
    50                  55                  60

Trp Ser Trp Ser Gly Gly Thr Asn Asn Val Lys Ser Tyr Pro Asn Ala
65                  70                  75                  80

Gly Leu Glu Phe Ser Arg Gly Lys Lys Val Ser Ser Ile Gly Thr Ile
                85                  90                  95

Asn Gly Gly Ala Asp Trp Asp Tyr Ser Gly Ser Asn Ile Arg Ala Asn
            100                 105                 110

Val Ala Tyr Gly Ile Phe Thr Ser Ala Asp Pro Asn His Val Thr Ser
        115                 120                 125

Ser Gly Asp Tyr Glu Leu Met Ile Trp Leu Gly Lys Leu Gly Asp Ile
    130                 135                 140

Tyr Pro Ile Gly Asn Ser Ile Gly Arg Val Glu Ala Ala Asn Arg Glu
145                 150                 155                 160

Trp Asp Phe Leu Val Gly Tyr Asn Gly Ala Met Lys Val Phe Ser Phe
                165                 170                 175

Val Ala Pro Ser Pro Val Thr Leu Phe Asp Gly Asn Ile Met Asp Phe
            180                 185                 190

Phe Tyr Val Met Arg Asp Met Gln Gly Tyr Pro Met Asp Lys Gln Tyr
        195                 200                 205

Leu Leu Ser Leu Gln Phe Gly Thr Glu Pro Phe Thr Gly Ser Asn Ala
    210                 215                 220

Asn Phe Ser Cys Trp Tyr Phe Gly Ala Lys Ile Lys
225                 230                 235
```

<210> SEQ ID NO 23
<211> LENGTH: 237
<212> TYPE: PRT
<213> ORGANISM: Gliocladium roseum (4)

<400> SEQUENCE: 23

```
Met Lys Thr Gly Ile Ala Tyr Leu Ala Ala Val Leu Pro Leu Ala Met
1               5                   10                  15
```

```
Ala Glu Ser Leu Cys Asp Gln Tyr Ala Tyr Leu Ser Arg Asp Gly Tyr
         20                  25                  30

Asn Phe Asn Asn Asn Glu Trp Gly Ala Ala Thr Gly Thr Gly Asp Gln
         35                  40                  45

Cys Thr Tyr Val Asp Ser Thr Ser Ser Gly Gly Val Ser Trp His Ser
 50                  55                  60

Asp Trp Thr Trp Ser Gly Ser Glu Ser Glu Ile Lys Ser Tyr Pro Tyr
 65                  70                  75                  80

Ser Gly Leu Asp Leu Pro Glu Lys Lys Ile Val Thr Ser Ile Gly Ser
                 85                  90                  95

Ile Ser Thr Gly Ala Glu Trp Ser Tyr Ser Gly Ser Asp Ile Arg Ala
                100                 105                 110

Asp Val Ala Tyr Asp Thr Phe Thr Ala Ala Asp Pro Asn His Ala Thr
             115                 120                 125

Ser Ser Gly Asp Tyr Glu Val Met Ile Trp Leu Ala Asn Leu Gly Gly
         130                 135                 140

Leu Thr Pro Ile Gly Ser Pro Ile Gly Thr Val Lys Ala Ala Gly Arg
145                 150                 155                 160

Asp Trp Glu Leu Trp Asp Gly Tyr Asn Gly Ala Met Arg Val Tyr Ser
                165                 170                 175

Phe Val Ala Pro Ser Gln Leu Asn Ser Phe Asp Gly Glu Ile Met Asp
             180                 185                 190

Phe Phe Tyr Val Val Lys Asp Met Arg Gly Phe Pro Ala Asp Ser Gln
         195                 200                 205

His Leu Leu Thr Val Gln Phe Gly Thr Glu Pro Ile Ser Gly Ser Gly
     210                 215                 220

Ala Lys Phe Ser Val Ser His Trp Ser Ala Lys Leu Gly
225                 230                 235

<210> SEQ ID NO 24
<211> LENGTH: 237
<212> TYPE: PRT
<213> ORGANISM: Memnoniella echinata

<400> SEQUENCE: 24

Met Lys Val Ala Ala Leu Leu Val Ala Leu Ser Pro Leu Ala Phe Ala
 1               5                  10                  15

Gln Ser Leu Cys Asp Gln Tyr Ser Tyr Tyr Ser Ser Asn Gly Tyr Glu
                 20                  25                  30

Phe Asn Asn Asn Met Trp Gly Arg Asn Ser Gly Gln Gly Asn Gln Cys
         35                  40                  45

Thr Tyr Val Asp Tyr Ser Ser Pro Asn Gly Val Gly Trp Arg Val Asn
 50                  55                  60

Trp Asn Trp Ser Gly Gly Asp Asn Asn Val Lys Ser Tyr Pro Tyr Ser
 65                  70                  75                  80

Gly Arg Gln Leu Pro Thr Lys Arg Ile Val Ser Trp Ile Gly Ser Leu
                 85                  90                  95

Pro Thr Thr Val Ser Trp Asn Tyr Gln Gly Asn Asn Leu Arg Ala Asn
                100                 105                 110

Val Ala Tyr Asp Leu Phe Thr Ala Ala Asn Pro Asn His Pro Asn Ser
             115                 120                 125

Ser Gly Asp Tyr Glu Leu Met Ile Trp Leu Gly Arg Leu Gly Asn Val
         130                 135                 140

Tyr Pro Ile Gly Asn Gln Val Ala Thr Val Asn Ile Ala Gly Gln Gln
145                 150                 155                 160
```

Trp Asn Leu Tyr Tyr Gly Tyr Asn Gly Ala Met Gln Val Tyr Ser Phe
                165                 170                 175

Val Ser Pro Asn Gln Leu Asn Tyr Phe Ser Gly Asn Val Lys Asp Phe
            180                 185                 190

Phe Thr Tyr Leu Gln Tyr Asn Arg Ala Tyr Pro Ala Asp Ser Gln Tyr
        195                 200                 205

Leu Ile Thr Tyr Gln Phe Gly Thr Glu Pro Phe Thr Gly Gln Asn Ala
    210                 215                 220

Val Phe Thr Val Ser Asn Trp Ser Ala Gln Gln Asn Asn
225                 230                 235

<210> SEQ ID NO 25
<211> LENGTH: 245
<212> TYPE: PRT
<213> ORGANISM: Emericella desertoru

<400> SEQUENCE: 25

Met Lys Leu Leu Ala Leu Ser Leu Val Ser Leu Ala Ser Ala Ala Ser
  1               5                  10                  15

Ala Ala Ser Ile Leu Ser Asn Thr Phe Thr Arg Arg Ser Asp Phe Cys
             20                  25                  30

Gly Gln Trp Asp Thr Ala Thr Val Gly Asn Phe Ile Val Tyr Asn Asn
         35                  40                  45

Leu Trp Gly Gln Asp Asn Ala Asp Ser Gly Ser Gln Thr Gly Val Asp
 50                  55                  60

Ser Ala Asn Gly Asn Ser Ile Ser Trp His Thr Thr Trp Ser Trp Ser
65                  70                  75                  80

Gly Gly Ser Ser Ser Val Lys Ser Tyr Ala Asn Ala Ala Tyr Gln Phe
                 85                  90                  95

Thr Ser Thr Lys Leu Asn Ser Leu Ser Ser Ile Pro Thr Ser Trp Lys
            100                 105                 110

Trp Gln Tyr Ser Thr Thr Asp Ile Val Ala Asn Val Ala Tyr Asp Leu
        115                 120                 125

Phe Thr Ser Ser Ser Ala Gly Gly Asp Ser Glu Tyr Glu Ile Met Ile
    130                 135                 140

Trp Leu Ala Ala Leu Gly Gly Ala Gly Pro Ile Ser Ser Thr Gly Ser
145                 150                 155                 160

Ser Ile Ala Thr Val Thr Leu Gly Gly Val Thr Trp Ser Leu Tyr Ser
                165                 170                 175

Gly Pro Asn Gly Ser Met Gln Val Tyr Ser Phe Val Ala Ser Ser Thr
            180                 185                 190

Thr Glu Ser Phe Ser Ala Asp Leu Met Asp Phe Ile Asn Tyr Leu Ala
        195                 200                 205

Glu Asn Gln Gly Leu Ser Ser Ser Gln Leu Thr His Val Gln Ala Gly
    210                 215                 220

Thr Glu Pro Phe Thr Gly Thr Asp Ala Thr Leu Thr Val Ser Ser Tyr
225                 230                 235                 240

Ser Val Ser Val Ser
                245

<210> SEQ ID NO 26
<211> LENGTH: 371
<212> TYPE: PRT
<213> ORGANISM: Actinomycete sp. 11AG8

<400> SEQUENCE: 26

Met Arg Ser His Pro Arg Ser Ala Thr Met Thr Val Leu Val Val Leu

```
                1               5                  10                 15
        Ala Ser Leu Gly Ala Leu Leu Thr Ala Ala Pro Ala Gln Ala Asn
                        20                 25                 30

Gln Gln Ile Cys Asp Arg Tyr Gly Thr Thr Ile Gln Asp Arg Tyr
                        35                 40                 45

Val Val Gln Asn Asn Arg Trp Gly Thr Ser Ala Thr Gln Cys Ile Asn
                        50                 55                 60

Val Thr Gly Asn Gly Phe Glu Ile Thr Gln Ala Asp Gly Ser Val Pro
        65                      70                 75                 80

Thr Asn Gly Ala Pro Lys Ser Tyr Pro Ser Val Tyr Asp Gly Cys His
                            85                 90                 95

Tyr Gly Asn Cys Ala Pro Arg Thr Thr Leu Pro Met Arg Ile Ser Ser
                            100                105                110

Ile Gly Ser Ala Pro Ser Ser Val Ser Tyr Arg Tyr Thr Gly Asn Gly
                            115                120                125

Val Tyr Asn Ala Ala Tyr Asp Ile Trp Leu Asp Pro Thr Pro Arg Thr
                    130                135                140

Asn Gly Val Asn Arg Thr Glu Ile Met Ile Trp Phe Asn Arg Val Gly
        145                     150                155                160

Pro Val Gln Pro Ile Gly Ser Pro Val Gly Thr Ala His Val Gly Gly
                            165                170                175

Arg Ser Trp Glu Val Trp Thr Gly Ser Asn Gly Ser Asn Asp Val Ile
                            180                185                190

Ser Phe Leu Ala Pro Ser Ala Ile Ser Ser Trp Ser Phe Asp Val Lys
                            195                200                205

Asp Phe Val Asp Gln Ala Val Ser His Gly Leu Ala Thr Pro Asp Trp
                    210                215                220

Tyr Leu Thr Ser Ile Gln Ala Gly Phe Glu Pro Trp Glu Gly Gly Thr
        225                     230                235                240

Gly Leu Ala Val Asn Ser Phe Ser Ala Val Asn Ala Gly Gly Gly
                            245                250                255

Asn Gly Gly Thr Pro Gly Thr Pro Ala Ala Cys Gln Val Ser Tyr Ser
                            260                265                270

Thr His Thr Trp Pro Gly Gly Phe Thr Val Asp Thr Thr Ile Thr Asn
                            275                280                285

Thr Gly Ser Thr Pro Val Asp Gly Trp Glu Leu Asp Phe Thr Leu Pro
                    290                295                300

Ala Gly His Thr Val Thr Ser Ala Trp Asn Ala Leu Ile Ser Pro Ala
        305                     310                315                320

Ser Gly Ala Val Thr Ala Arg Ser Thr Gly Ser Asn Gly Arg Ile Ala
                            325                330                335

Ala Asn Gly Gly Thr Gln Ser Phe Gly Phe Gln Gly Thr Ser Ser Gly
                            340                345                350

Thr Gly Phe Asn Ala Pro Ala Gly Gly Arg Leu Asn Gly Thr Ser Cys
                            355                360                365

Thr Val Arg
            370

<210> SEQ ID NO 27
<211> LENGTH: 381
<212> TYPE: PRT
<213> ORGANISM: Streptomyces lividans

<400> SEQUENCE: 27

Met Arg Thr Leu Arg Pro Gln Ala Arg Ala Pro Arg Gly Leu Leu Ala
```

```
            1               5                  10                  15
Ala Leu Gly Ala Val Leu Ala Ala Phe Ala Leu Val Ser Ser Leu Val
                    20                  25                  30

Thr Ala Ala Ala Pro Ala Gln Ala Asp Thr Thr Ile Cys Glu Pro Phe
                35                  40                  45

Gly Thr Thr Thr Ile Gln Gly Arg Tyr Val Val Gln Asn Asn Arg Trp
            50                  55                  60

Gly Ser Thr Ala Pro Gln Cys Val Thr Ala Thr Asp Thr Gly Phe Arg
65                  70                  75                  80

Val Thr Gln Ala Asp Gly Ser Ala Pro Thr Asn Gly Ala Pro Lys Ser
                85                  90                  95

Tyr Pro Ser Val Phe Asn Gly Cys His Tyr Thr Asn Cys Ser Pro Gly
                100                 105                 110

Thr Asp Leu Pro Val Arg Leu Asp Thr Val Ser Ala Ala Pro Ser Ser
                115                 120                 125

Ile Ser Tyr Gly Phe Val Asp Gly Ala Val Tyr Asn Ala Ser Tyr Asp
            130                 135                 140

Ile Trp Leu Asp Pro Thr Ala Arg Thr Asp Gly Val Asn Gln Thr Glu
145                 150                 155                 160

Ile Met Ile Trp Phe Asn Arg Val Gly Pro Ile Gln Pro Ile Gly Ser
                165                 170                 175

Pro Val Gly Thr Ala Ser Val Gly Gly Arg Thr Trp Glu Val Trp Ser
                180                 185                 190

Gly Gly Asn Gly Ser Asn Asp Val Leu Ser Phe Val Ala Pro Ser Ala
            195                 200                 205

Ile Ser Gly Trp Ser Phe Asp Val Met Asp Phe Val Arg Ala Thr Val
            210                 215                 220

Ala Arg Gly Leu Ala Glu Asn Asp Trp Tyr Leu Thr Ser Val Gln Ala
225                 230                 235                 240

Gly Phe Glu Pro Trp Gln Asn Gly Ala Gly Leu Ala Val Asn Ser Phe
                245                 250                 255

Ser Ser Thr Val Glu Thr Gly Thr Pro Gly Gly Thr Asp Pro Gly Asp
                260                 265                 270

Pro Gly Gly Pro Ser Ala Cys Ala Val Ser Tyr Gly Thr Asn Val Trp
            275                 280                 285

Gln Asp Gly Phe Thr Ala Asp Val Thr Val Thr Asn Thr Gly Thr Ala
            290                 295                 300

Pro Val Asp Gly Trp Gln Leu Ala Phe Thr Leu Pro Ser Gly Gln Arg
305                 310                 315                 320

Ile Thr Asn Ala Trp Asn Ala Ser Leu Thr Pro Ser Ser Gly Ser Val
                325                 330                 335

Thr Ala Thr Gly Ala Ser His Asn Ala Arg Ile Ala Pro Gly Gly Ser
                340                 345                 350

Leu Ser Phe Gly Phe Gln Gly Thr Tyr Gly Gly Ala Phe Ala Glu Pro
            355                 360                 365

Thr Gly Phe Arg Leu Asn Gly Thr Ala Cys Thr Thr Val
370                 375                 380

<210> SEQ ID NO 28
<211> LENGTH: 260
<212> TYPE: PRT
<213> ORGANISM: Rhodothermus marinus

<400> SEQUENCE: 28

Met Asn Val Met Arg Ala Val Leu Val Leu Ser Leu Leu Leu Leu Phe
```

```
                 1               5                  10                  15
Gly Cys Asp Trp Leu Phe Pro Asp Gly Asp Asn Gly Lys Glu Pro Glu
                20                  25                  30

Pro Glu Pro Glu Pro Thr Val Glu Leu Cys Gly Arg Trp Asp Ala Arg
            35                  40                  45

Asp Val Ala Gly Gly Arg Tyr Arg Val Ile Asn Asn Val Trp Gly Ala
        50                  55                  60

Glu Thr Ala Gln Cys Ile Glu Val Gly Leu Thr Gly Asn Phe Thr
65                  70                  75                  80

Ile Thr Arg Ala Asp His Asp Asn Gly Asn Asn Val Ala Ala Tyr Pro
                85                  90                  95

Ala Ile Tyr Phe Gly Cys His Trp Ala Pro Ala Arg Ala Ile Arg Asp
            100                 105                 110

Cys Ala Ala Arg Ala Gly Ala Val Arg Arg Ala His Glu Leu Asp Val
        115                 120                 125

Thr Pro Ile Thr Thr Gly Arg Trp Asn Ala Ala Tyr Asp Ile Trp Phe
    130                 135                 140

Ser Pro Val Thr Asn Ser Gly Asn Gly Tyr Ser Gly Gly Ala Glu Leu
145                 150                 155                 160

Met Ile Trp Leu Asn Trp Asn Gly Gly Val Met Pro Gly Gly Ser Arg
                165                 170                 175

Val Ala Thr Val Glu Leu Ala Gly Ala Thr Trp Glu Val Trp Tyr Ala
            180                 185                 190

Asp Trp Asp Trp Asn Tyr Ile Ala Tyr Arg Arg Thr Thr Pro Thr Thr
        195                 200                 205

Ser Val Ser Glu Leu Asp Leu Lys Ala Phe Ile Asp Asp Ala Val Ala
    210                 215                 220

Arg Gly Tyr Ile Arg Pro Glu Trp Tyr Leu His Ala Val Glu Thr Gly
225                 230                 235                 240

Phe Glu Leu Trp Glu Gly Gly Ala Gly Leu Arg Thr Ala Asp Phe Ser
                245                 250                 255

Val Thr Val Gln
            260

<210> SEQ ID NO 29
<211> LENGTH: 264
<212> TYPE: PRT
<213> ORGANISM: Erwinia carotovara

<400> SEQUENCE: 29

Met Gln Thr Val Asn Thr Gln Pro His Arg Ile Phe Arg Val Leu Leu
1               5                   10                  15

Pro Ala Val Phe Ser Ser Leu Leu Leu Ser Ser Leu Thr Val Ser Ala
            20                  25                  30

Ala Ser Ser Ser Asn Asp Ala Asp Lys Leu Tyr Phe Gly Asn Asn Lys
        35                  40                  45

Tyr Tyr Leu Phe Asn Asn Val Trp Gly Lys Asp Glu Ile Lys Gly Trp
    50                  55                  60

Gln Gln Thr Ile Phe Tyr Asn Ser Pro Ile Ser Met Gly Trp Asn Trp
65                  70                  75                  80

His Trp Pro Ser Ser Thr His Ser Val Lys Ala Tyr Pro Ser Leu Val
                85                  90                  95

Ser Gly Trp His Trp Thr Ala Gly Tyr Thr Glu Asn Ser Gly Leu Pro
            100                 105                 110

Ile Gln Leu Ser Ser Asn Lys Ser Ile Thr Ser Asn Val Thr Tyr Ser
```

```
                115                 120                 125
Ile Lys Ala Thr Gly Thr Tyr Asn Ala Ala Tyr Asp Ile Trp Phe His
            130                 135                 140

Thr Thr Asp Lys Ala Asn Trp Asp Ser Ser Pro Thr Asp Glu Leu Met
145                 150                 155                 160

Ile Trp Leu Asn Asp Thr Asn Ala Gly Pro Ala Gly Asp Tyr Ile Glu
                165                 170                 175

Thr Val Phe Leu Gly Asp Ser Ser Trp Asn Val Phe Lys Gly Trp Ile
            180                 185                 190

Asn Ala Asp Asn Gly Gly Gly Trp Asn Val Phe Ser Phe Val His Thr
            195                 200                 205

Ser Gly Thr Asn Ser Ala Ser Leu Asn Ile Arg His Phe Thr Asp Tyr
        210                 215                 220

Leu Val Gln Thr Lys Gln Trp Met Ser Asp Glu Lys Tyr Ile Ser Ser
225                 230                 235                 240

Val Glu Phe Gly Thr Glu Ile Phe Gly Gly Asp Gly Gln Ile Asp Ile
                245                 250                 255

Thr Glu Trp Arg Val Asp Val Lys
            260

<210> SEQ ID NO 30
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 9
<223> OTHER INFORMATION: n = A,T,C or G

<400> SEQUENCE: 30
aayaayytnt gggg                                                    14

<210> SEQ ID NO 31
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 9
<223> OTHER INFORMATION: n = A,T,C or G

<400> SEQUENCE: 31
caraayytnt gggg                                                    14

<210> SEQ ID NO 32
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 12
<223> OTHER INFORMATION: n = inosine

<400> SEQUENCE: 32
aayaayaayh wntgggg                                                 17

<210> SEQ ID NO 33
<211> LENGTH: 15
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 6
<223> OTHER INFORMATION: n = A,T,C or G

<400> SEQUENCE: 33
garytnatga thtgg                                                      15

<210> SEQ ID NO 34
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 10
<223> OTHER INFORMATION: n = A,T,C or G

<400> SEQUENCE: 34
ccadatcatn arytc                                                      15

<210> SEQ ID NO 35
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 9
<223> OTHER INFORMATION: n = inosine

<400> SEQUENCE: 35
taygarytna tgathtgg                                                   18

<210> SEQ ID NO 36
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 10
<223> OTHER INFORMATION: n = inosine

<400> SEQUENCE: 36
ccadatcatn arytcrta                                                   18

<210> SEQ ID NO 37
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 6
<223> OTHER INFORMATION: n = A,T,C or G

<400> SEQUENCE: 37
gtraanggyt crgtrcc                                                    17

<210> SEQ ID NO 38
<211> LENGTH: 17
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 6
<223> OTHER INFORMATION: n = A,T,C or G

<400> SEQUENCE: 38
gtraanggyt crgtycc                                               17

<210> SEQ ID NO 39
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 6
<223> OTHER INFORMATION: n = A,T,C or G

<400> SEQUENCE: 39
gtraanggyt cygtrcc                                               17

<210> SEQ ID NO 40
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 6
<223> OTHER INFORMATION: n = A,T,C or G

<400> SEQUENCE: 40
gtraanggyt cygtycc                                               17

<210> SEQ ID NO 41
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 12, 15
<223> OTHER INFORMATION: n = A,T,C or G

<400> SEQUENCE: 41
gtraarcayt cngtncc                                               17

<210> SEQ ID NO 42
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 1
<223> OTHER INFORMATION: Xaa = Ser, Tyr, Cys, Trp, Thr, Asn, Lys, or Arg
<220> FEATURE:
<221> NAME/KEY: VARIANT
<222> LOCATION: 2
<223> OTHER INFORMATION: Xaa = Val or Pro
<220> FEATURE:
<221> NAME/KEY: VARIANT
<222> LOCATION: 3
<223> OTHER INFORMATION: Xaa = Lys or Ala
```

```
<220> FEATURE:
<221> NAME/KEY: VARIANT
<222> LOCATION: 4
<223> OTHER INFORMATION: Xaa = Ser or Ala
<220> FEATURE:
<221> NAME/KEY: VARIANT
<222> LOCATION: 5
<223> OTHER INFORMATION: Xaa = Tyr or Phe

<400> SEQUENCE: 42

Xaa Xaa Xaa Xaa Xaa
 1               5

<210> SEQ ID NO 43
<211> LENGTH: 102
<212> TYPE: PRT
<213> ORGANISM: Trichoderma reesei

<400> SEQUENCE: 43

Asn Asn Leu Trp Gly Ala Ser Ala Gly Ser Gly Phe Gly Cys Val Thr
 1               5                  10                  15

Ala Val Ser Leu Ser Gly Gly Ala Ser Trp His Ala Asp Trp Gln Trp
             20                  25                  30

Ser Gly Gly Gln Asn Asn Val Lys Ser Tyr Gln Asn Ser Gln Ile Ala
         35                  40                  45

Ile Pro Gln Lys Arg Thr Val Asn Ser Ile Ser Ser Met Pro Thr Thr
 50                  55                  60

Ala Ser Trp Ser Tyr Ser Gly Ser Asn Ile Arg Ala Asn Val Ala Tyr
 65                  70                  75                  80

Asp Leu Phe Thr Ala Ala Asn Pro Asn His Val Thr Tyr Ser Gly Asp
                 85                  90                  95

Tyr Glu Leu Met Ile Trp
            100

<210> SEQ ID NO 44
<211> LENGTH: 104
<212> TYPE: PRT
<213> ORGANISM: Fusarium equiseti

<400> SEQUENCE: 44

Asn Asn Phe Trp Gly Lys Asp Ser Gly Thr Gly Asp Gln Cys Thr His
 1               5                  10                  15

Val Asn Trp Asn Asn Ala Asn Gly Ala Gly Trp Asp Val Glu Trp Asn
             20                  25                  30

Trp Ser Gly Gly Lys Asp Asn Val Lys Ser Tyr Pro Asn Ser Ala Leu
         35                  40                  45

Leu Ile Gly Glu Asp Lys Lys Thr Ile Ser Ser Ile Thr Asn Met Gln
 50                  55                  60

Ser Thr Ala Glu Trp Lys Tyr Ser Gly Asp Asn Leu Arg Ala Asp Val
 65                  70                  75                  80

Ala Tyr Asp Leu Phe Thr Ala Ala Asp Pro Asn His Glu Thr Ser Ser
                 85                  90                  95

Gly Glu Tyr Glu Leu Met Ile Trp
            100

<210> SEQ ID NO 45
<211> LENGTH: 103
<212> TYPE: PRT
<213> ORGANISM: Gliocladium roseum

<400> SEQUENCE: 45
```

```
Asn Asn Lys Trp Gly Gln Gly Ser Gly Ser Gln Cys Leu Thr
1               5                   10                  15

Ile Asp Lys Thr Trp Asp Ser Asn Val Ala Phe His Ala Asp Trp Ser
                20                  25                  30

Trp Ser Gly Gly Thr Asn Asn Val Lys Ser Tyr Pro Lys Arg Arg Ser
            35                  40                  45

Glu Phe Ser Arg Gly Lys Lys Val Ser Ser Ile Gly Thr Ile Asn Gly
50                  55                  60

Gly Ala Asp Trp Asp Tyr Ser Gly Ser Asn Ile Arg Ala Asn Val Ala
65                  70                  75                  80

Tyr Gly Ile Phe Thr Ser Ala Asp Pro Asn His Val Thr Ser Ser Gly
                85                  90                  95

Asp Tyr Glu Leu Met Ile Trp
            100
```

```
<210> SEQ ID NO 46
<211> LENGTH: 89
<212> TYPE: PRT
<213> ORGANISM: Artificial Sequence
<220> FEATURE:
<223> OTHER INFORMATION: hypothetical Acremonium brachypenium peptide
      without intron

<400> SEQUENCE: 46

Trp Gly Pro Arg Ser Ala Glu Ser Gly Glu Gln Cys Thr Thr Asn Asn
1               5                   10                  15

Gly Leu Ser Asp Asp Gly Thr Leu Ser Trp Ser Val Glu Trp Thr Trp
                20                  25                  30

Val Gly Ala Pro Ser Ser Val Lys Ser Tyr Pro Asn Val Phe Val Glu
            35                  40                  45

Ala Glu Pro Arg Pro Leu Ser Glu Val Ser Ser Ile Gln Ala Glu Trp
50                  55                  60

Ala Trp Thr Tyr Ser Gly Ala Gly Asp Phe Thr Thr Asn Val Ala Phe
65                  70                  75                  80

Asp Ile Phe Thr Gly Glu Thr Ala Asp
                85
```

```
<210> SEQ ID NO 47
<211> LENGTH: 102
<212> TYPE: PRT
<213> ORGANISM: Aspergillus kawachii (1)

<400> SEQUENCE: 47

Gln Asn Leu Trp Gly Glu Tyr Gln Gly Thr Gly Ser Gln Cys Val Tyr
1               5                   10                  15

Val Asp Lys Leu Ser Ser Ser Gly Ala Ser Trp His Thr Lys Trp Thr
                20                  25                  30

Trp Ser Gly Gly Glu Gly Thr Val Lys Ser Tyr Ser Asn Ser Gly Leu
            35                  40                  45

Thr Phe Asp Lys Lys Leu Val Ser Asp Val Ser Ser Ile Pro Thr Ser
50                  55                  60

Val Thr Trp Ser Gln Asp Asp Thr Asn Val Gln Ala Asp Val Ser Tyr
65                  70                  75                  80

Asp Leu Phe Thr Ala Ala Asn Ala Asp His Ala Thr Ser Ser Gly Asp
                85                  90                  95

Tyr Glu Leu Met Ile Trp
            100
```

```
<210> SEQ ID NO 48
<211> LENGTH: 102
<212> TYPE: PRT
<213> ORGANISM: Aspergillus aculeatus

<400> SEQUENCE: 48

Asn Asn Leu Trp Gly Lys Asp Ala Gly Ser Gly Ser Gln Cys Thr Thr
 1               5                  10                  15

Val Asn Ser Ala Ser Ser Ala Gly Thr Ser Trp Ser Thr Lys Trp Asn
            20                  25                  30

Trp Ser Gly Gly Glu Asn Ser Val Lys Ser Tyr Ala Asn Ser Gly Leu
        35                  40                  45

Thr Phe Asn Lys Lys Leu Val Ser Gln Ile Ser Gln Ile Pro Thr Thr
 50                  55                  60

Ala Arg Trp Ser Tyr Asp Asn Thr Gly Ile Arg Ala Asp Val Ala Tyr
 65                  70                  75                  80

Asp Leu Phe Thr Ala Ala Asp Ile Asn His Val Thr Trp Ser Gly Asp
                85                  90                  95

Tyr Glu Leu Met Ile Trp
            100

<210> SEQ ID NO 49
<211> LENGTH: 104
<212> TYPE: PRT
<213> ORGANISM: Humicola insolens

<400> SEQUENCE: 49

Asn Asn Leu Trp Gly Lys Asp Thr Ala Thr Ser Gly Trp Gln Cys Thr
 1               5                  10                  15

Tyr Leu Asp Gly Thr Asn Asn Gly Gly Ile Gln Trp Ser Thr Ala Trp
            20                  25                  30

Glu Trp Gln Gly Ala Pro Asp Asn Val Lys Ser Tyr Pro Tyr Val Gly
        35                  40                  45

Lys Gln Ile Gln Arg Gly Arg Lys Ile Ser Asp Ile Asn Ser Met Arg
 50                  55                  60

Thr Ser Val Ser Trp Thr Tyr Asp Arg Thr Asp Ile Arg Ala Asn Val
 65                  70                  75                  80

Ala Tyr Asp Val Phe Thr Ala Arg Asp Pro Asp His Pro Asn Trp Gly
                85                  90                  95

Gly Asp Tyr Glu Leu Met Ile Trp
            100

<210> SEQ ID NO 50
<211> LENGTH: 104
<212> TYPE: PRT
<213> ORGANISM: Actinomycte sp.11AG8

<400> SEQUENCE: 50

Asn Asn Arg Trp Gly Thr Ser Ala Thr Gln Cys Ile Asn Val Thr Gly
 1               5                  10                  15

Asn Gly Phe Glu Ile Thr Gln Ala Asp Gly Ser Val Pro Thr Asn Gly
            20                  25                  30

Ala Pro Lys Ser Tyr Pro Ser Val Tyr Asp Gly Cys His Tyr Gly Asn
        35                  40                  45

Cys Ala Pro Arg Thr Thr Leu Pro Met Arg Ile Ser Ser Ile Gly Ser
 50                  55                  60

Ala Pro Ser Ser Val Ser Tyr Arg Tyr Thr Gly Asn Gly Val Tyr Asn
 65                  70                  75                  80
```

```
Ala Ala Tyr Asp Ile Trp Leu Asp Pro Thr Pro Arg Thr Asn Gly Val
            85                  90                  95

Asn Arg Thr Glu Ile Met Ile Trp
        100
```

<210> SEQ ID NO 51
<211> LENGTH: 110
<212> TYPE: PRT
<213> ORGANISM: Erwinia carotovara

<400> SEQUENCE: 51

```
Asn Asn Val Trp Gly Lys Asp Glu Ile Lys Gly Trp Gln Gln Thr Ile
1               5                   10                  15

Phe Tyr Asn Ser Pro Ile Ser Met Gly Trp Asn Trp His Trp Pro Ser
            20                  25                  30

Ser Thr His Ser Val Lys Ala Tyr Pro Ser Leu Val Ser Gly Trp His
        35                  40                  45

Trp Thr Ala Gly Tyr Thr Glu Asn Ser Gly Leu Pro Ile Gln Leu Ser
    50                  55                  60

Ser Asn Lys Ser Ile Thr Ser Asn Val Thr Tyr Ser Ile Lys Ala Thr
65                  70                  75                  80

Gly Thr Tyr Asn Ala Ala Tyr Asp Ile Trp Phe His Thr Thr Asp Lys
                85                  90                  95

Ala Asn Trp Asp Ser Ser Pro Thr Asp Glu Leu Met Ile Trp
            100                 105                 110
```

<210> SEQ ID NO 52
<211> LENGTH: 103
<212> TYPE: PRT
<213> ORGANISM: Gliocladium roseum

<400> SEQUENCE: 52

```
Asn Asn Leu Trp Gly Met Gly Ser Gly Ser Gly Ser Gln Cys Thr Tyr
1               5                   10                  15

Val Asp Lys Val Trp Ala Glu Gly Val Ala Trp His Thr Asp Trp Ser
            20                  25                  30

Trp Ser Gly Gly Asp Asn Asn Val Lys Ser Tyr Pro Tyr Ser Gly Arg
        35                  40                  45

Glu Leu Gly Thr Lys Arg Ile Val Ser Ile Lys Ser Ile Ser Ser
    50                  55                  60

Gly Ala Asp Trp Asp Tyr Thr Gly Ser Asn Leu Arg Ala Asn Ala Ala
65                  70                  75                  80

Tyr Asp Ile Phe Thr Ser Ala Asn Pro Asn His Ala Thr Ser Ser Gly
                85                  90                  95

Asp Tyr Glu Leu Met Ile Trp
            100
```

<210> SEQ ID NO 53
<211> LENGTH: 100
<212> TYPE: PRT
<213> ORGANISM: Artificial Sequence
<220> FEATURE:
<223> OTHER INFORMATION: hypothetical Gliocladium roseum peptide
      without intron

<400> SEQUENCE: 53

```
Asn Asn Leu Trp Gly Gln Asp Asn Gly Ser Gly Ser Gln Cys Leu Thr
1               5                   10                  15

Val Glu Gly Val Thr Asp Gly Leu Ala Ala Trp Ser Ser Thr Trp Ser
            20                  25                  30
```

-continued

Trp Ser Gly Gly Ser Ser Val Lys Ser Tyr Ser Asn Ala Val Leu
            35                  40                  45

Ser Ala Glu Ala Ala Arg Ile Ser Ala Ile Ser Ser Ile Pro Ser Lys
 50                  55                  60

Trp Glu Trp Arg Ser Tyr Thr Gly Thr Asp Ile Val Ala Asn Val Ala
 65                  70                  75                  80

Tyr Asp Leu Phe Ser Asn Thr Asp Cys Gly Asp Thr Pro Glu Tyr Glu
                 85                  90                  95

Leu Met Ile Trp
            100

<210> SEQ ID NO 54
<211> LENGTH: 104
<212> TYPE: PRT
<213> ORGANISM: Humicola grisea

<400> SEQUENCE: 54

Asn Asn Leu Trp Gly Gln Asp Thr Ala Thr Ser Gly Trp Gln Cys Thr
 1               5                  10                  15

Tyr Leu Asp Gly Thr Asn Asn Gly Gly Ile Gln Trp Ser Thr Ala Trp
             20                  25                  30

Glu Trp Gln Gly Ala Pro Asp Asn Val Lys Ser Tyr Pro Tyr Val Gly
            35                  40                  45

Lys Gln Ile Gln Arg Gly Arg Lys Ile Ser Asp Ile Asn Ser Met Arg
 50                  55                  60

Thr Ser Val Ser Trp Thr Tyr Asp Arg Thr Asp Ile Arg Ala Asn Val
 65                  70                  75                  80

Ala Tyr Asp Val Phe Thr Ala Arg Asp Pro Asp His Pro Asn Trp Gly
                 85                  90                  95

Gly Asp Tyr Glu Phe Met Ile Trp
            100

<210> SEQ ID NO 55
<211> LENGTH: 105
<212> TYPE: PRT
<213> ORGANISM: Rhodothermus marinus

<400> SEQUENCE: 55

Asn Asn Val Trp Gly Ala Glu Thr Ala Gln Cys Ile Glu Val Gly Leu
 1               5                  10                  15

Glu Thr Gly Asn Phe Thr Ile Thr Arg Ala Asp His Asp Asn Gly Asn
             20                  25                  30

Asn Val Ala Ala Tyr Pro Ala Ile Tyr Phe Gly Cys His Trp Ala Pro
            35                  40                  45

Ala Arg Ala Ile Arg Asp Cys Ala Arg Ala Gly Ala Val Arg Arg
 50                  55                  60

Ala His Glu Leu Asp Val Thr Pro Ile Thr Thr Gly Arg Trp Asn Ala
 65                  70                  75                  80

Ala Tyr Asp Ile Trp Phe Ser Pro Val Thr Asn Ser Gly Asn Gly Tyr
                 85                  90                  95

Ser Gly Gly Ala Glu Leu Met Ile Trp
            100                 105

<210> SEQ ID NO 56
<211> LENGTH: 104
<212> TYPE: PRT
<213> ORGANISM: Streptomyces lividans -continued

```
<400> SEQUENCE: 56

Asn Asn Arg Trp Gly Ser Thr Ala Pro Gln Cys Val Thr Ala Thr Asp
1               5                   10                  15

Thr Gly Phe Arg Val Thr Gln Ala Asp Gly Ser Ala Pro Thr Asn Gly
            20                  25                  30

Ala Pro Lys Ser Tyr Pro Ser Val Phe Asn Gly Cys His Tyr Thr Asn
        35                  40                  45

Cys Ser Pro Gly Thr Asp Leu Pro Val Arg Leu Asp Thr Val Ser Ala
50                  55                  60

Ala Pro Ser Ser Ile Ser Tyr Gly Phe Val Asp Gly Ala Val Tyr Asn
65                  70                  75                  80

Ala Ser Tyr Asp Ile Trp Leu Asp Pro Thr Ala Arg Thr Asp Gly Val
                85                  90                  95

Asn Gln Thr Glu Ile Met Ile Trp
            100

<210> SEQ ID NO 57
<211> LENGTH: 96
<212> TYPE: PRT
<213> ORGANISM: Penicillium notatum

<400> SEQUENCE: 57

Trp Gly Lys Asp Ser Gly Ser Gly Ser Gln Cys Ala Ser Val Asn Ser
1               5                   10                  15

Ile Ser Asp Ser Gly Val Ser Trp Ser Thr Thr Trp Asn Trp Ser Gly
            20                  25                  30

Gly Glu Asp Asn Val Lys Ser Tyr Pro Asn Ser Gly Leu Val Ala Leu
        35                  40                  45

Lys Lys Gln Pro Val Ser Asp Ile Ser Ser Ile Pro Ser Ser Val Lys
50                  55                  60

Trp Asn Tyr Asp Asn Thr Asp Ile Arg Ala Asp Val Ala Tyr Asp Leu
65                  70                  75                  80

Phe Thr Ala Ala Asp Ile Asn His Asp Thr Ser Ser Gly Asp Tyr Glu
                85                  90                  95

<210> SEQ ID NO 58
<211> LENGTH: 87
<212> TYPE: PRT
<213> ORGANISM: Artificial Sequence
<220> FEATURE:
<223> OTHER INFORMATION: hypothetical Phanerochaete chrysosporium
      peptide without intron

<400> SEQUENCE: 58

Trp Gly Lys Asp Ser Gly Thr Gly Ser Gln Cys Leu Thr Val Asp Gly
1               5                   10                  15

Ile Ser Ser Gly Leu Leu Lys Trp Ser Ala Thr Trp Ser Trp Ser Gly
            20                  25                  30

Gly Pro Tyr Asn Val Lys Ser Tyr Pro Asn Ala Val Leu Gln Ala Pro
        35                  40                  45

Ala Ala Arg Ala Ser Ala Ile Ser Ser Ile Pro Ser Lys Trp Gln Trp
        50                  55                  60

Glu Ser Tyr Thr Gly Ser Asn Val Ile Ala Asn Val Ala Tyr Asp Leu
65                  70                  75                  80

Phe Ser Asn Ser Asp Cys Gly
                85

<210> SEQ ID NO 59
```

<211> LENGTH: 84
<212> TYPE: PRT
<213> ORGANISM: Artificial Sequence
<220> FEATURE:
<223> OTHER INFORMATION: hypothetical F42 peptide without intron

<400> SEQUENCE: 59

Ser Gln Cys Thr Thr Phe Glu Ser Leu Ser Gly Asn Thr Ile Val Trp
1               5                   10                  15
Asn Thr Lys Trp Ser Trp Ser Gly Gly Gln Gly Gln Val Lys Ser Phe
            20                  25                  30
Ala Asn Ala Ala Leu Gln Phe Thr Pro Lys Lys Leu Ser Ser Val Lys
        35                  40                  45
Ser Ile Asp Ser Thr Trp Lys Trp Lys Ser Tyr Ser Gly Ser Asn Ile
    50                  55                  60
Val Ala Asp Val Ala Tyr Asp Met Phe Leu Ser Thr Ser Pro Gly Gly
65                  70                  75                  80
Asp His Asn Tyr

<210> SEQ ID NO 60
<211> LENGTH: 100
<212> TYPE: PRT
<213> ORGANISM: Artificial Sequence
<220> FEATURE:
<223> OTHER INFORMATION: hypothetical Emericella desertoru peptide
      without intron
<220> FEATURE:
<221> NAME/KEY: VARIANT
<222> LOCATION: 6
<223> OTHER INFORMATION: Xaa = Any Amino Acid

<400> SEQUENCE: 60

Asn Asn Leu Trp Gly Xaa Asp Asn Ala Asp Ser Gly Ser Gln Cys Thr
1               5                   10                  15
Gly Val Asp Ser Ala Asn Gly Asn Ser Ile Ser Trp His Thr Thr Trp
            20                  25                  30
Ser Trp Ser Gly Gly Ser Ser Val Lys Ser Tyr Ala Asn Ala Ala
        35                  40                  45
Tyr Gln Phe Thr Ser Thr Lys Leu Asn Ser Leu Ser Ser Ile Pro Thr
    50                  55                  60
Ser Trp Lys Trp Gln Tyr Ser Thr Thr Asp Ile Val Ala Asn Val Ala
65                  70                  75                  80
Tyr Asp Leu Phe Thr Ser Ser Ser Ala Gly Gly Asp Ser Glu Tyr Glu
                85                  90                  95
Phe Met Ile Trp
            100

<210> SEQ ID NO 61
<211> LENGTH: 27
<212> TYPE: PRT
<213> ORGANISM: Myceliopthora thermophilia

<400> SEQUENCE: 61

Ala Asn Val Ala Tyr Asp Leu Phe Thr Ala Ala Asp Pro Asn His Ala
1               5                   10                  15
Thr Ser Ser Gly Asp Tyr Glu Leu Met Ile Trp
            20                  25

<210> SEQ ID NO 62
<211> LENGTH: 104
<212> TYPE: PRT
<213> ORGANISM: Chaetomium brasilliense

```
<400> SEQUENCE: 62

Asn Asn Phe Trp Gly Gln Ser Arg Ala Thr Ser Gly Ser Gln Cys Thr
  1               5                  10                  15

Tyr Leu Asp Ser Ser Asn Ser Gly Ile His Trp Thr His Thr Thr Trp
             20                  25                  30

Thr Trp Glu Gly Gly Glu Gly Glu Val Lys Ser Tyr Ala Tyr Ser Gly
         35                  40                  45

Arg Gln Val Ser Thr Gly Leu Thr Ile Ala Ser Ile Asp Ser Met Gln
 50                  55                  60

Thr Ser Val Ser Trp Glu Tyr Asn Thr Thr Asp Ile Gln Ala Asn Val
 65                  70                  75                  80

Ala Tyr Asp Ile Phe Thr Ala Glu Asp Pro Asp His Glu His Ser Ser
             85                  90                  95

Gly Asp Tyr Glu Leu Met Ile Trp
            100

<210> SEQ ID NO 63
<211> LENGTH: 102
<212> TYPE: PRT
<213> ORGANISM: Artificial Sequence
<220> FEATURE:
<223> OTHER INFORMATION: EGIII consensus sequence

<400> SEQUENCE: 63

Asn Asn Leu Trp Gly Lys Asp Ser Gly Gly Ser Gln Cys Thr Thr Val
  1               5                  10                  15

Asp Ser Leu Ser Asp Gly Gly Ile Ser Trp Ser Thr Ala Trp Ser Trp
             20                  25                  30

Ser Gly Gly Glu Gly Asn Val Lys Ser Tyr Pro Asn Ser Gly Leu Gln
         35                  40                  45

Phe Ser Ala Gly Lys Lys Val Ser Ser Ile Ser Ile Pro Ser Ser
 50                  55                  60

Ala Ser Trp Val Tyr Ser Gly Thr Asp Ile Arg Ala Asn Val Ala Tyr
 65                  70                  75                  80

Asp Leu Phe Thr Ala Ala Asp Pro Asn His Ala Thr Ser Ser Gly Asp
             85                  90                  95

Tyr Glu Leu Met Ile Trp
            100

<210> SEQ ID NO 64
<211> LENGTH: 5
<212> TYPE: PRT
<213> ORGANISM: Artificial Sequence
<220> FEATURE:
<223> OTHER INFORMATION: BOX 1 peptide
<220> FEATURE:
<221> NAME/KEY: VARIANT
<222> LOCATION: 1
<223> OTHER INFORMATION: Xaa = Asn or Gln

<400> SEQUENCE: 64

Xaa Asn Leu Trp Gly
  1               5

<210> SEQ ID NO 65
<211> LENGTH: 6
<212> TYPE: PRT
<213> ORGANISM: Artificial Sequence
<220> FEATURE:
<223> OTHER INFORMATION: BOX 1' peptide
<220> FEATURE:
```

```
<221> NAME/KEY: VARIANT
<222> LOCATION: 4
<223> OTHER INFORMATION: Xaa = Phe, Leu, Tyr, Ile, Leu, Asn, or Lys

<400> SEQUENCE: 65

Asn Asn Asn Xaa Trp Gly
 1               5

<210> SEQ ID NO 66
<211> LENGTH: 5
<212> TYPE: PRT
<213> ORGANISM: Artificial Sequence
<220> FEATURE:
<223> OTHER INFORMATION: BOX 2 peptide

<400> SEQUENCE: 66

Glu Leu Met Ile Trp
 1               5

<210> SEQ ID NO 67
<211> LENGTH: 6
<212> TYPE: PRT
<213> ORGANISM: Artificial Sequence
<220> FEATURE:
<223> OTHER INFORMATION: BOX 2' peptide

<400> SEQUENCE: 67

Tyr Glu Leu Met Ile Trp
 1               5

<210> SEQ ID NO 68
<211> LENGTH: 6
<212> TYPE: PRT
<213> ORGANISM: Artificial Sequence
<220> FEATURE:
<223> OTHER INFORMATION: BOX 3 peptide
<220> FEATURE:
<221> NAME/KEY: VARIANT
<222> LOCATION: 4
<223> OTHER INFORMATION: Xaa = Pro or Cys

<400> SEQUENCE: 68

Gly Thr Glu Xaa Phe Thr
 1               5
```